US012674154B2

(12) United States Patent
Li et al.

(10) Patent No.: US 12,674,154 B2
(45) Date of Patent: Jul. 7, 2026

(54) FUSION PROTEIN THAT IMPROVES GENE EDITING EFFICIENCY AND APPLICATION THEREOF

(71) Applicants: EAST CHINA NORMAL UNIVERSITY, Shanghai (CN); BRL MEDICINE INC., Shanghai (CN)

(72) Inventors: Dali Li, Shanghai (CN); Xiaohui Zhang, Shanghai (CN); Mingyao Liu, Shanghai (CN); Biyun Zhu, Shanghai (CN); Liang Chen, Shanghai (CN)

(73) Assignees: EAST CHINA NORMAL UNIVERSITY, Shanghai (CN); BRL Medicine (Shanghai) Co., Ltd., Shanghai (CN)

( * ) Notice: Subject to any disclaimer, the term of this patent is extended or adjusted under 35 U.S.C. 154(b) by 1028 days.

(21) Appl. No.: 17/843,462

(22) Filed: Jun. 17, 2022

(65) Prior Publication Data

US 2022/0364072 A1      Nov. 17, 2022

Related U.S. Application Data

(63) Continuation-in-part of application No. PCT/CN2020/137239, filed on Dec. 17, 2020.

(30) Foreign Application Priority Data

Dec. 18, 2019   (CN) .......................... 201911310969.8
Dec. 18, 2019   (CN) .......................... 201911312537.0
Dec. 18, 2019   (CN) .......................... 201911312544.0

(51) Int. Cl.
| | |
|---|---|
| *C12N 9/78* | (2006.01) |
| *A01K 67/0275* | (2024.01) |
| *A61K 38/46* | (2006.01) |
| *A61K 38/50* | (2006.01) |
| *A61K 48/00* | (2006.01) |
| *A61K 49/00* | (2006.01) |
| *C12N 9/22* | (2006.01) |
| *C12N 15/11* | (2006.01) |
| *C12N 15/90* | (2006.01) |

(52) U.S. Cl.
CPC ............ *C12N 9/78* (2013.01); *A01K 67/0275* (2013.01); *A61K 38/465* (2013.01); *A61K 38/50* (2013.01); *A61K 49/0008* (2013.01); *C12N 9/22* (2013.01); *C12N 15/11* (2013.01); *C12N 15/907* (2013.01); *C12Y 305/04001* (2013.01); *C12Y 305/04004* (2013.01); *A01K 2217/05* (2013.01); *A01K 2217/07* (2013.01); *A01K 2227/105* (2013.01); *A01K 2267/0306* (2013.01); *A61K 48/00* (2013.01); *C07K*

*2319/09* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 11,274,288 B2 | 3/2022 | Baram et al. | |
| 2015/0166981 A1* | 6/2015 | Kromor ................. | A61P 25/00 |
| 2018/0230494 A1 | 8/2018 | Joung et al. | |
| 2020/0255857 A1 | 8/2020 | Gori et al. | |

FOREIGN PATENT DOCUMENTS

| | | |
|---|---|---|
| CN | 105647968 A | 6/2016 |
| CN | 108350449 A | 7/2018 |
| CN | 108513575 A | 9/2018 |
| CN | 108588182 A | 9/2018 |
| CN | 108707635 A | 10/2018 |
| CN | 109021111 A | 12/2018 |
| CN | 109153994 A | 1/2019 |
| CN | 109880851 A | 6/2019 |
| WO | WO-2010132092 A2 | 11/2010 |

(Continued)

OTHER PUBLICATIONS

Anders et al., Structural plasticity of PAM recognition by engineered variants of the RNA guided endonuclease variants of the RNA guided endonuclease Cas9 Mol. Cell (Year: 2016).*

(Continued)

*Primary Examiner* — Tracy Vivlemore
*Assistant Examiner* — John David Moore
(74) *Attorney, Agent, or Firm* — Harness, Dickey & Pierce, P.L.C.

(57) ABSTRACT

Provided are a fusion protein that improves gene editing efficiency and an application thereof. The fusion protein comprises a single-stranded DNA binding protein functional domain, nucleoside deaminase and nuclease. According to CBEs, when carrying our base conversion from C-G to T-A, nucleoside deaminase such as cytosine deaminase carries out deamination by using single-stranded DNA as a substrate, and by re-fusing the single-stranded DNA binding protein functional domain on the fusion protein of the nucleoside deaminase and nuclease, the chance of single-stranded DNA being exposed to the nucleoside deaminase is greatly increased, thereby significantly improving base editing efficiency. The present disclosure provides a breakthrough improvement of single-base gene editing technology and can greatly promote the application thereof in aspects such as gene editing, gene therapy, cell therapy, animal model making, and crop genetic breeding.

49 Claims, 10 Drawing Sheets

Specification includes a Sequence Listing.

(56) References Cited

FOREIGN PATENT DOCUMENTS

| WO | PCT/US 2014 033082 | * | 4/2014 |
|----|----|----|----|
| WO | WO-2017040348 A1 | | 3/2017 |
| WO | WO-2017070632 A2 | | 4/2017 |
| WO | WO-2017142923 A1 | | 8/2017 |
| WO | WO-2018176009 A1 | | 9/2018 |
| WO | WO-2018209158 A2 | | 11/2018 |

OTHER PUBLICATIONS

Bockerev "From RPA to CRCA2: lessons from single-stranded DNA binding by the OB-fold" Current Opinion of Structural Biology (Year: 2004).*

Ming Lei et al., "DNA self-recognition in the strucutre of POT1 bound to telomeric single-stranded DNA" Nature (Year: 2003).*

Xiao Wang et al., "Efficient base editing in methylated regions with a huma APOBEC3A Cas9 Fusion" Nature Biotechnology (Year: 2018).*

Romero et al., "CRISPR to fix bad blood: a new tool in basic and clinical hematology" Haematologica, March (Year: 2019).*

Lee et al., "Gene editing with CRISPR-Cas9 for treating beta-hemaglobinopathies" Blood (Year: 2015).*

Ching Wang et al., "Using structural based protein engineering to modulate the different inhibition effects of SAUGI on human and HSV uracil DNA glycosylase" Nucleic Acids Research (Year: 2016).*

Komor et al., "Improved base excision repair inhibition and bateriaphage Mu Gam protein yields C: G to T: A base editors with higher efficiency and product purity" Science Advances (Year: 2017).*

Jan. 15, 2024 Supplementary European Search Report Application No. 20903960.1.

Oct. 10, 2023 First Office Action issued in Japanese Patent Application No. 2022-538379 with English translation.

May 14, 2024 Rejection issued in Japanese Patent Application No. 2022-538379.

Natsuo Kawamoto et al., Safety assessment and poential regulation of genome-edited insects, Sanshi-Konchu Biotec vol. 86 No. 2 pp. 125-132.

Mar. 16, 2021 International Search Report issued in International Patent Application No. PCT/CN2020/137239.

Mar. 16, 2021 Written Opinion of the International Searching Authority issued in International Patent Application No. PCT/CN2020/137239.

Chuai,G. et al. "Deep CRISPR: optimized CRISPR guide RNA design by deep learning" Genome Biology, vol. 19, Dec. 31, 2018, Article No. 80.

Havlicek,S. et al. "Re-engineered RNA-Guided FokI-Nucleases for Improved Genome Editing in Human Cells" Molecular Therapy, vol. 25, No. 2, Feb. 28, 2017, pp. 342-355.

Koblan,L.W. et al. "Improving cytidine and adenine base editors by expression optimization and ancestral reconstruction" nature biotechnology, vol. 36, No. 9, May 29, 2018, pp. 843-848.

Zhang,X.H. et al. "Increasing the efficiency and targeting range of cytidine base editors through fusion of a single-stranded DNA-binding protein domain" Nature Cell Biology, vol. 22, Jun. 30, 2020 (Jun. 30, 2020), pp. 740-750.

D7-Xiaohui Zhang, The optimization and application of base editing technology, Basic Science Series of China Doctoral Dissertation Database, Issue 8, Aug. 15, 2020, full text.

Gehrke,J.M. et al. "An APOBEC3A-Cas9 base editor with minimized bystander and off-target activities" nature biotechnology, vol. 36, No. 10, Oct. 31, 2018, pp. 977-984.

Oct. 9, 2021 Chinese First Office Action issued in Chinese Patent Application No. 2019113109698.

Sep. 28 2021 Chinese First Office Action issued in Chinese Patent Application No. 2019113125370.

Jan. 28, 2022 Chinese Second Office Action issued in Chinese Patent Application No. 2019113125370.

May 30, 2022 Chinese Third Office Action issued in Chinese Patent Application No. 2019113125370.

Oct. 11, 2021 Chinese First Office Action issued in Chinese Patent Application No. 2019113125440.

"Improving cytidine and adenine base editors by expression optimization and ancestral reconstruction" , Koblan,L.W. et al., Nat Biotechnol, vol. 36, No. 9, Oct. 31, 2018), pp. 843-846.

"Chain A, Rad51 (N-Terminal Domain), Accession IB22-A", Aihara,H. et al., GenBank Oct. 10, 2012.

"Chain C, Replication Protein A 70 Kda Dna-binding Submit, Accession IL10-C", Bochkareva,E. et al., GenBank Oct. 9, 2012.

Probable DNA dC->dU-editing enzyme APOBEC-3A[*Homo sapiens*], GenBank, NCBI, NP 001180218, May 4, 2019.

Priority application text of CN 2019113109698(CN112979821B).

Priority application text of CN 2019113125370(CN112979822A).

Priority application text of CN 2019113125440(CN112979823B).

* cited by examiner

A3A-BE4max

| NLS | hA3A | spCas9n | UGI | UGI | NLS | hyA3A-BE4max

| NLS | hA3A | rad51 | spCas9n | UGI | UGI | NLS |

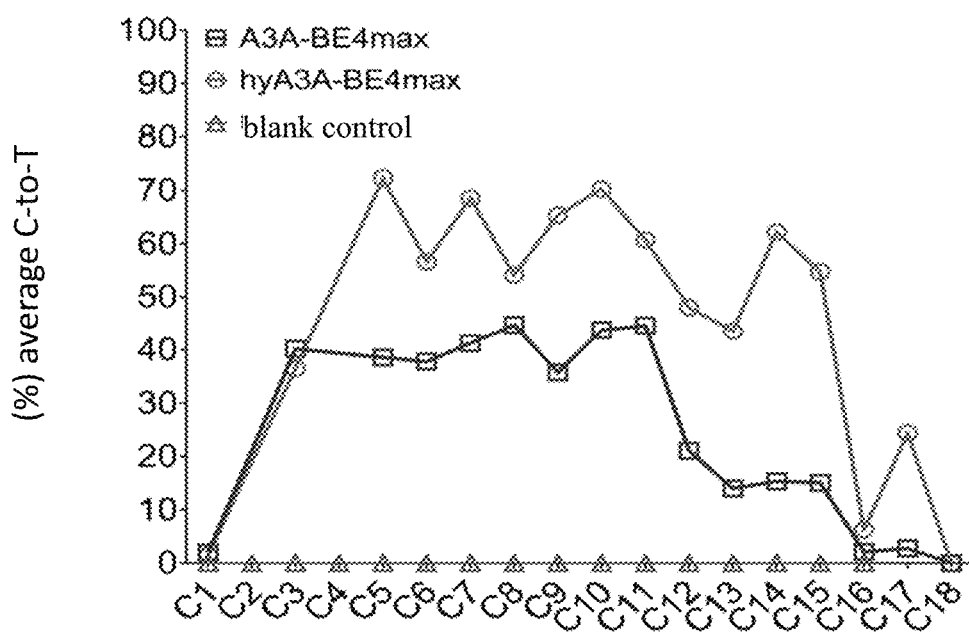
Fig. 7
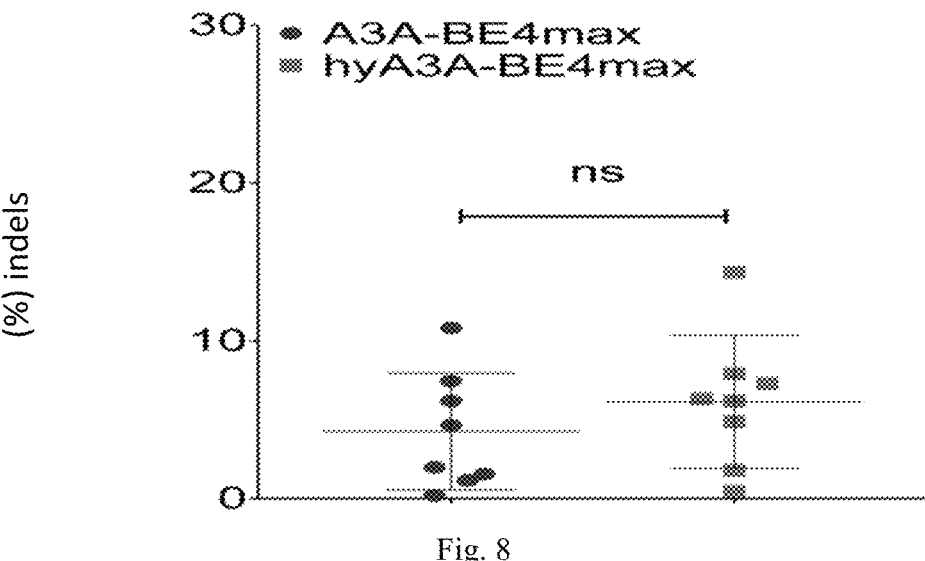
Fig. 8
eA3A-BE4max
| NLS | A3A N57G | spCas9n | UGI | UGI | NLS |
hyeA3A-BE4max
| NLS | A3A N57G | Rad51DBD | spCas9n | UGI | UGI | NLS |
Fig. 9

A3A-BE4max-DMD-sg3

Frequency (%)

Wt    ATCTGACATCTCATCAAGGACTTGTTGGTAATC

AD08   ATCTGACATTTATTAAGGACTTGTTGGTAATG   45(S393F, H394Y,Q395stop)
       ATCTGACAT----------AGGACTTGTTGGTAATG   5.02(-7bp)
AD11   ATCTGAAATCTCATCAAGGACTTGTTGGTAATG   90.85(T392K)
AD14   ATCTGACATTTATTAAGGACTTGTTGGTAATG   15.9(S393F, H394Y,Q395stop)
       ATCTGACAT----------AGGACTTGTTGGTAATG   3.11(-7bp)
AD16   ATCTGACAT----------AAGGACTTGTTGGTAATG   43.55(-6bp)
AD20   ATCTGACATTTATTAAGGACTTGTTGGTAATG   19.43(S393F, H394Y,Q395stop)
       ATCTGACAT----------AGGACTTGTTGGTAATG   7.24(-7bp)
       ATCTGACATGTCATCAAGGACTTGTTGGTAATG   6.74(S393C)
AD26   ATCTGACATTTCATTAAGGACTTGTTGGTAATG   24.12(S393F, Q395stop)
AD27   ATCTGACATTTCATCAAGGACTTGTTGGTAATG   62.99(S393F)
       ATCTGACATTTTATTAAGGACTTGTTGGTAATG   3.12(S393F, H394Y,Q395stop)
AD35   ATCTGATATCTCATTAAGGACTTGTTGGTAATG   42.93(T392I, Q395stop)
       ATCTGACATTTCATTAAGGACTTGTTGGTAATG   23.49(S393F, Q395stop)
AD39   ATCTGACATCTCATGAAGGACTTGTTGGTAATG   23.17(Q395E)
       ATCTGACATTTTATTAAGGACTTGTTGGTAATG   2.67(S393F, H394Y,Q395stop)
AD45   ATCTGACATTTCATCAAGGACTTGTTGGTAATG   76.94(S393F)
       ATCTGACATTTTATTAAGGACTTGTTGGTAATG   16.87(S393F, H394Y,Q395stop)
       ATCTGACAT----------AGGACTTGTTGGTAATG   2.24(-7bp)
AD48   ATCTGATATCTCATCAAGGACTTGTTGGTAATG   36.07(T392I)

hyA3A-BE4max-DMD-sg3

Frequency (%)

Wt    ATCTGACATCTCATCAAGGACTTGTTGGTAATG

BD02   ATCTGACATC-----TTAAAGACTTGTTGGTAATG   28.93 (-3bp, G396R )
       ATCTGACATCTTATTAAGGACTTGTTGGTAATG   23.52 (H394Y,Q395stop)
       ATCTGACATC---ATTAAGGACTTGTTGGTAATG   14.65 (-2bp, Q395stop )
       ATCTGACATTTAATCAAGGACTTGTTGGTAATG   9.8(S393F, H394N)
       ATCTGACATTTAATTAAGGACTTGTTGGTAATG   8 (S393F, H394N,Q395stop)
       ATCTGACATTTTATTAAGGACTTGTTGGTAATG   7.8 (S393F, H394Y,Q395stop)
BD03   ATCTGACATTTAATTAAGGACTTGTTGGTAATG   98.65 (S393F, H394N,Q395stop)
BD04   ATCTGACATTTAATCAAGGACTTGTTGGTAATG   97.49 (S393F, H394N)
BD05   ATCTGACATTTTATTAAGGACTTGTTGGTAATG   84.98 (S393F, H394Y,Q395stop)
       ATCTGACAT----------AGGACTTGTTGGTAATG   13.0 (-7bp)
BD06   ATCTGACATC-----TCAAGAACTTGTTGGTAATG   97.1(-3bp, G396E)
       ATCTGACATTTTATTAAGGACTTGTTGGTAATG   1.76 (S393F, H394Y,Q395stop)
BD07   ATCTGACATTTTATTAAGGACTTGTTGGTAATG   96.71 (S393F, H394Y,Q395stop)
BD09   ATCTGACA---TCATTAAGGACTTGTTGGTAATG   19.31 (-2bp, Q395stop )
       ATCTGACATC-----TTAAAGACTTGTTGGTAATG   14.74(-3bp, G396R )
       ATCTGACATTTTATTAAGGACTTGTTGGTAATG   12.50 (S393F, H394Y,Q395stop)
       ATCTGACATCTTATTAAGGACTTGTTGGTAATG   8.1(H394Y,Q395stop)
       ATCTGACATTTTATGAAGGACTTGTTGGTAATG   3.9(S393F, H394Y,Q395E)
       ATCTGACATTTAATTAAGGACTTGTTGGTAATG   3.5(S393F, H394N,Q395stop)
BD12   ATCTGACATTTTATTAAGGACTTGTTGGTAATG   99.32 (S393F, H394Y,Q395stop)
BD15   ATCTGACA---TCATTAAGGACTTGTTGGTAATG   96.30 (-2bp, Q395stop )
BD16   ATCTGACATCTTATTAAGGACTTGTTGGTAATG   98.74 (H394Y,Q395stop)

Fig. 19

SEQUENCE LISTING

<160> NUMBER OF SEQ ID NOS: 36

<210> SEQ ID NO 1
<211> LENGTH: 114
<212> TYPE: PRT
<213> ORGANISM: Homo sapiens

<400> SEQUENCE: 1

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln

<210> SEQ ID NO 2
<211> LENGTH: 342
<212> TYPE: DNA
<213> ORGANISM: Homo sapiens

<400> SEQUENCE: 2
atggcaatgc agatgcagct tgaagcaaat gcagatactt cagtggaaga agaaagcttt        60
ggcccacaac ccatttcacg gttagagcag tgtggcataa atgccaacga tgtgaagaaa       120
ttggaagaag ctggattcca tactgtggag gctgttgcct atgcgccaaa gaaggagcta       180

-continued

--- ataaatatta agggaattag tgaagccaaa gctgataaaa ttctggctga ggcagctaaa          240
ttagttccaa tgggtttcac cactgcaact gaattccacc aaaggcggtc agagatcata          300
cagattacta ctggctccaa agagcttgac aaactacttc aa                             342

<210> SEQ ID NO 3
<211> LENGTH: 228
<212> TYPE: PRT
<213> ORGANISM: Rattus norvegicus

<400> SEQUENCE: 3

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
                100                 105                 110

Ile Tyr Ile Ala Arg Leu Tyr His His Ala Asp Pro Arg Asn Arg Gln
            115                 120                 125

Gly Leu Arg Asp Leu Ile Ser Ser Gly Val Thr Ile Gln Ile Met Thr
            130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Pro Gln Leu Thr Phe Phe Thr Ile Ala
            195                 200                 205

Leu Gln Ser Cys His Tyr Gln Arg Leu Pro Pro His Ile Leu Trp Ala
    210                 215                 220

Thr Gly Leu Lys
225

<210> SEQ ID NO 4
<211> LENGTH: 684
<212> TYPE: DNA
<213> ORGANISM: Rattus norvegicus

<400> SEQUENCE: 4
tcctcagaga ctgggcctgt cgccgtcgat ccaaccctgc gccgccggat tgaacctcac           60
gagtttgaag tgttctttga cccccgggag ctgagaaagg agacatgcct gctgtacgag          120
atcaactggg gaggcaggca ctccatctgg aggcacacct ctcagaacac aaataagcac          180
gtggaggtga acttcatcga gaagtttacc acagagcggt acttctgccc caataccaga          240
tgtagcatca catggtttct gagctggtcc ccttgcggag agtgtagcag ggccatcacc          300
gagttcctgt ccagatatcc acacgtgaca ctgtttatct catcgccag gctgtatcac          360

-continued

```
cacgcagacc caaggaatag gcagggcctg cgcgatctga tcagctccgg cgtgaccatc       420
cagatcatga cagagcagga gtccggctac tgctggcgga acttcgtgaa ttattctcct       480
agcaacgagg cccactggcc taggtaccca cacctgtggg tgcgcctgta cgtgctggag       540
ctgtattgca tcatcctggg cctgcccct tgtctgaata tcctgcggag aaagcagccc        600
cagctgacct tctttacaat cgccctgcag tcttgtcact atcagaggct gccacccac        660 atcctgtggg ccacaggcct gaag                                             684
```

```
<210> SEQ ID NO 5
<211> LENGTH: 1367
<212> TYPE: PRT
<213> ORGANISM: Streptococcus pyogenes

<400> SEQUENCE: 5

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
        210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
        290                 295                 300

Leu Arg Val Asn Thr Glu Ile Thr Lys Ala Pro Leu Ser Ala Ser Met
305                 310                 315                 320
```

-continued

```
Ile Lys Arg Tyr Asp Glu His His Gln Asp Leu Thr Leu Leu Lys Ala
                325             330             335

Leu Val Arg Gln Gln Leu Pro Glu Lys Tyr Lys Glu Ile Phe Phe Asp
            340             345             350

Gln Ser Lys Asn Gly Tyr Ala Gly Tyr Ile Asp Gly Gly Ala Ser Gln
        355             360             365

Glu Glu Phe Tyr Lys Phe Ile Lys Pro Ile Leu Glu Lys Met Asp Gly
    370             375             380

Thr Glu Glu Leu Leu Val Lys Leu Asn Arg Glu Asp Leu Leu Arg Lys
385             390             395             400

Gln Arg Thr Phe Asp Asn Gly Ser Ile Pro His Gln Ile His Leu Gly
            405             410             415

Glu Leu His Ala Ile Leu Arg Arg Gln Glu Asp Phe Tyr Pro Phe Leu
            420             425             430

Lys Asp Asn Arg Glu Lys Ile Glu Lys Ile Leu Thr Phe Arg Ile Pro
            435             440             445

Tyr Tyr Val Gly Pro Leu Ala Arg Gly Asn Ser Arg Phe Ala Trp Met
    450             455             460

Thr Arg Lys Ser Glu Glu Thr Ile Thr Pro Trp Asn Phe Glu Glu Val
465             470             475             480

Val Asp Lys Gly Ala Ser Ala Gln Ser Phe Ile Glu Arg Met Thr Asn
            485             490             495

Phe Asp Lys Asn Leu Pro Asn Glu Lys Val Leu Pro Lys His Ser Leu
            500             505             510

Leu Tyr Glu Tyr Phe Thr Val Tyr Asn Glu Leu Thr Lys Val Lys Tyr
            515             520             525

Val Thr Glu Gly Met Arg Lys Pro Ala Phe Leu Ser Gly Glu Gln Lys
    530             535             540

Lys Ala Ile Val Asp Leu Leu Phe Lys Thr Asn Arg Lys Val Thr Val
545             550             555             560

Lys Gln Leu Lys Glu Asp Tyr Phe Lys Lys Ile Glu Cys Phe Asp Ser
            565             570             575

Val Glu Ile Ser Gly Val Glu Asp Arg Phe Asn Ala Ser Leu Gly Thr
            580             585             590

Tyr His Asp Leu Leu Lys Ile Ile Lys Asp Lys Asp Phe Leu Asp Asn
            595             600             605

Glu Glu Asn Glu Asp Ile Leu Glu Asp Ile Val Leu Thr Leu Thr Leu
            610             615             620

Phe Glu Asp Arg Glu Met Ile Glu Glu Arg Leu Lys Thr Tyr Ala His
625             630             635             640

Leu Phe Asp Asp Lys Val Met Lys Gln Leu Lys Arg Arg Arg Tyr Thr
            645             650             655

Gly Trp Gly Arg Leu Ser Arg Lys Leu Ile Asn Gly Ile Arg Asp Lys
            660             665             670

Gln Ser Gly Lys Thr Ile Leu Asp Phe Leu Lys Ser Asp Gly Phe Ala
            675             680             685

Asn Arg Asn Phe Met Gln Leu Ile His Asp Asp Ser Leu Thr Phe Lys
            690             695             700

Glu Asp Ile Gln Lys Ala Gln Val Ser Gly Gln Gly Asp Ser Leu His
705             710             715             720

Glu His Ile Ala Asn Leu Ala Gly Ser Pro Ala Ile Lys Lys Gly Ile
            725             730             735
```

```
Leu Gln Thr Val Lys Val Val Asp Glu Leu Val Lys Val Met Gly Arg
        740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
```

```
        1145                 1150                 1155

Val Lys  Glu Leu Leu Gly Ile  Thr Ile Met Glu Arg  Ser Ser Phe
    1160                 1165                 1170

Glu Lys  Asn Pro Ile Asp Phe  Leu Glu Ala Lys Gly  Tyr Lys Glu
    1175                 1180                 1185

Val Lys  Lys Asp Leu Ile Ile  Lys Leu Pro Lys Tyr  Ser Leu Phe
    1190                 1195                 1200

Glu Leu  Glu Asn Gly Arg Lys  Arg Met Leu Ala Ser  Ala Gly Glu
    1205                 1210                 1215

Leu Gln  Lys Gly Asn Glu Leu  Ala Leu Pro Ser Lys  Tyr Val Asn
    1220                 1225                 1230

Phe Leu  Tyr Leu Ala Ser His  Tyr Glu Lys Leu Lys  Gly Ser Pro
    1235                 1240                 1245

Glu Asp  Asn Glu Gln Lys Gln  Leu Phe Val Glu Gln  His Lys His
    1250                 1255                 1260

Tyr Leu  Asp Glu Ile Ile Glu  Gln Ile Ser Glu Phe  Ser Lys Arg
    1265                 1270                 1275

Val Ile  Leu Ala Asp Ala Asn  Leu Asp Lys Val Leu  Ser Ala Tyr
    1280                 1285                 1290

Asn Lys  His Arg Asp Lys Pro  Ile Arg Glu Gln Ala  Glu Asn Ile
    1295                 1300                 1305

Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365

<210> SEQ ID NO 6
<211> LENGTH: 4101
<212> TYPE: DNA
<213> ORGANISM: Streptococcus pyogenes

<400> SEQUENCE: 6
gacaagaagt acagcatcgg cctggccatc ggcaccaact ctgtgggctg ggccgtgatc        60
accgacgagt acaaggtgcc cagcaagaaa ttcaaggtgc tgggcaacac cgaccggcac       120
agcatcaaga gaaacctgat cggagccctg ctgttcgaca cgggcgaaac agccgaggcc       180
acccggctga agagaaccgc cagaagaaga tacaccagac ggaagaaccg gatctgctat       240
ctgcaagaga tcttcagcaa cgagatggcc aaggtggacg acagcttctt ccacagactg       300
gaagagtcct tcctggtgga agaggataag aagcacgagc ggcaccccat cttcggcaac       360
atcgtggacg aggtggccta ccacgagaag taccccacca tctaccacct gagaaagaaa       420
ctggtggaca gcaccgacaa ggccgacctg cggctgatct atctggccct ggcccacatg       480
atcaagttcc ggggccactt cctgatcgag ggcgacctga accccgacaa cagcgacgtg       540
gacaagctgt tcatccagct ggtgcagacc tacaaccagc tgttcgagga aaaccccatc       600
aacgccagcg gcgtggacgc caaggccatc ctgtctgcca gactgagcaa gagcagacgg       660
ctggaaaatc tgatcgccca gctgcccggc gagaagaaga tggcctgtt cggaaacctg       720 attgccctga gctggggcct gacccccaac ttcaagagca cttcgacct ggccgaggat       780 gccaaactgc agctgagcaa ggacacctac gacgacgacc tggacaacct gctggcccag       840
```

```
atcggcgacc agtacgccga cctgtttctg gccgccaaga acctgtccga cgccatcctg        900
ctgagcgaca tcctgagagt gaacaccgag atcaccaagg cccccctgag cgcctctatg        960
atcaagagat acgacgagca ccaccaggac ctgaccctgc tgaaagctct cgtgcggcag       1020
cagctgcctg agaagtacaa agagatttttc ttcgaccaga gcaagaacgg ctacgccggc      1080
tacattgacg gcggagccag ccaggaagag ttctacaagt tcatcaagcc catcctggaa       1140
aagatggacg gcaccgagga actgctcgtg aagctgaaca gagaggacct gctgcggaag       1200
cagcggacct tcgacaacgg cagcatcccc caccagatcc acctgggaga gctgcacgcc       1260
attctgcggc ggcaggaaga tttttaccca ttcctgaagg acaaccggga aaagatcgag       1320
aagatcctga ccttccgcat ccctactac gtgggccctc tggccagggg aaacagcaga        1380
ttcgcctgga tgaccagaaa gagcgaggaa accatcaccc cctggaactt cgaggaagtg       1440
gtggacaagg gcgcttccgc ccagagcttc atcgagcgga tgaccaactt cgataagaac       1500
ctgcccaacg agaaggtgct gcccaagcac agcctgctgt acgagtactt caccgtgtat       1560
aacgagctga ccaaagtgaa atacgtgacc gagggaatga gaaagcccgc cttcctgagc       1620
ggcgagcaga aaaaggccat cgtggacctg ctgttcaaga ccaaccggaa agtgaccgtg       1680
aagcagctga agaggacta cttcaagaaa atcgagtgct tcgactccgt ggaaatctcc        1740
ggcgtggaag atcggttcaa cgcctccctg ggcacatacc acgatctgct gaaaattatc       1800
aaggacaagg acttcctgga caatgaggaa aacgaggaca ttctggaaga tatcgtgctg       1860
accctgacac tgtttgagga cagagagatg atcgaggaac ggctgaaaac ctatgcccac       1920
ctgttcgacg acaaagtgat gaagcagctg aagcggcgga gatacaccgg ctggggcagg       1980
ctgagccgga agctgatcaa cggcatccgg gacaagcagt ccggcaagac aatcctggat       2040
ttcctgaagt ccgacggctt cgccaacaga aacttcatgc agctgatcca cgacgacagc       2100 ctgacctttta aagaggacat ccagaaagcc caggtgtccg gccagggcga tagcctgcac       2160
gagcacattg ccaatctggc cggcagcccc gccattaaga agggcatcct gcagacagtg        2220
aaggtggtgg acgagctcgt gaaagtgatg ggccggcaca gcccgagaa catcgtgatc        2280 gaaatggcca gagagaacca gaccacccag aagggacaga agaacagccg cgagagaatg       2340
aagcggatcg aagagggcat caaagagctg ggcagccaga tcctgaaaga acaccccgtg       2400
gaaaacaccc agctgcagaa cgagaagctg tacctgtact acctgcagaa tgggcgggat       2460
atgtacgtgg accaggaact ggacatcaac cggctgtccg actacgatgt ggaccatatc       2520
gtgcctcaga gctttctgaa ggacgactcc atcgacaaca aggtgctgac cagaagcgac       2580
aagaaccggg gcaagagcga caacgtgccc tccgaagagg tcgtgaagaa gatgaagaac       2640
tactggcggc agctgctgaa cgccaagctg attacccaga gaaagttcga caatctgacc       2700
aaggccgaga gaggcggcct gagcgaactg gataaggccg gcttcatcaa gagacagctg       2760
gtggaaaccc ggcagatcac aaagcacgtg gcacagatcc tggactcccg gatgaacact       2820
aagtacgacg agaatgacaa gctgatccgg gaagtgaaag tgatcaccct gaagtccaag       2880
ctggtgtccg atttccggaa ggatttccag ttttacaaag tgcgcgagat caacaactac       2940
caccacgccc acgacgccta cctgaacgcc gtcgtggaa ccgccctgat caaaaagtac        3000
cctaagctgg aaagcgagtt cgtgtacggc gactacaagg tgtacgacgt gcggaagatg       3060
atcgccaaga gcgagcagga aatcggcaag gctaccgcca agtacttctt ctacagcaac       3120
atcatgaact ttttcaagac cgagattacc ctggccaacg gcgagatccg gaagcggcct       3180
```

-continued

```
ctgatcgaga caaacggcga aaccggggag atcgtgtggg ataagggccg ggattttgcc      3240
accgtgcgga aagtgctgag catgccccaa gtgaatatcg tgaaaaagac cgaggtgcag      3300
acaggcggct tcagcaaaga gtctatcctg cccaagagga acagcgataa gctgatcgcc      3360
agaaagaagg actgggaccc taagaagtac ggcggcttcg acagccccac cgtggcctat      3420
tctgtgctgg tggtggccaa agtggaaaag ggcaagtcca agaaactgaa gagtgtgaaa      3480
gagctgctgg ggatcaccat catggaaaga agcagcttcg agaagaatcc catcgacttt      3540
ctggaagcca agggctacaa agaagtgaaa aaggacctga tcatcaagct gcctaagtac      3600
tccctgttcg agctggaaaa cggccggaag agaatgctgg cctctgccgg cgaactgcag      3660
aagggaaacg aactggccct gccctccaaa tatgtgaact tcctgtacct ggccagccac      3720
tatgagaagc tgaagggctc ccccgaggat aatgagcaga acagctgtt tgtggaacag      3780 cacaagcact acctggacga gatcatcgag cagatcagcg agttctccaa gagagtgatc      3840
ctggccgacg ctaatctgga caaagtgctg tccgcctaca acaagcaccg ggataagccc      3900
atcagagagc aggccgagaa tatcatccac ctgtttaccc tgaccaatct gggagcccct      3960
gccgccttca gtactttga caccaccatc gaccggaaga ggtacaccag caccaaagag      4020
gtgctggacg ccaccctgat ccaccagagc atcaccggcc tgtacgagac acggatcgac      4080
ctgtctcagc tgggaggtga c                                               4101

<210> SEQ ID NO 7
<211> LENGTH: 18
<212> TYPE: PRT
<213> ORGANISM: Artificial Sequence
<220> FEATURE:
<223> OTHER INFORMATION: Synthetic construct NLS

<400> SEQUENCE: 7

Lys Arg Thr Ala Asp Gly Ser Glu Phe Glu Ser Pro Lys Lys Lys Arg
1               5                   10                  15

Lys Val

<210> SEQ ID NO 8
<211> LENGTH: 54
<212> TYPE: DNA
<213> ORGANISM: Artificial Sequence
<220> FEATURE:
<223> OTHER INFORMATION: Synthetic construct NLS

<400> SEQUENCE: 8
aaacggacag ccgacggaag cgagttcgag tcaccaaaga agaagcggaa agtc            54

<210> SEQ ID NO 9
<211> LENGTH: 176
<212> TYPE: PRT
<213> ORGANISM: Bacillus subtilis

<400> SEQUENCE: 9

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60
```

-continued

```
Lys Pro Trp Ala Leu Val Ile Gln Asp Ser Asn Gly Glu Asn Lys Ile
65                  70                  75                  80

Lys Met Leu Ser Gly Gly Ser Gly Gly Ser Gly Gly Ser Thr Asn Leu
                85                  90                  95

Ser Asp Ile Ile Glu Lys Glu Thr Gly Lys Gln Leu Val Ile Gln Glu
            100                 105                 110

Ser Ile Leu Met Leu Pro Glu Glu Val Glu Glu Val Ile Gly Asn Lys
            115                 120                 125

Pro Glu Ser Asp Ile Leu Val His Thr Ala Tyr Asp Glu Ser Thr Asp
        130                 135                 140

Glu Asn Val Met Leu Leu Thr Ser Asp Ala Pro Glu Tyr Lys Pro Trp
145                 150                 155                 160

Ala Leu Val Ile Gln Asp Ser Asn Gly Glu Asn Lys Ile Lys Met Leu
                165                 170                 175
```

```
<210> SEQ ID NO 10
<211> LENGTH: 528
<212> TYPE: DNA
<213> ORGANISM: Bacillus subtilis

<400> SEQUENCE: 10
actaatctga gcgacatcat tgagaaggag actgggaaac agctggtcat tcaggagtcc        60
atcctgatgc tgcctgagga ggtggaggaa gtgatcggca acaagccaga gtctgacatc       120
ctggtgcaca ccgcctacga cgagtccaca gatgagaatg tgatgctgct gacctctgac       180
gcccccgagt ataagccttg ggccctggtc atccaggatt ctaacggcga gaataagatc       240
aagatgctga gcggaggatc cggaggatct ggaggcagca ccaacctgtc tgacatcatc       300
gagaaggaga caggcaagca gctggtcatc caggagagca tcctgatgct gcccgaagaa       360
gtcgaagaag tgatcggaaa caagcctgag agcgatatcc tggtccatac cgcctacgac       420
gagagtaccg acgaaaatgt gatgctgctg acatccgacg cccccagagta taagccctgg      480 gctctggtca tccaggattc caacggagag aacaaaatca aaatgctg                     528
```

```
<210> SEQ ID NO 11
<211> LENGTH: 181
<212> TYPE: PRT
<213> ORGANISM: Homo sapiens

<400> SEQUENCE: 11

Gly Gly Ser Asn Thr Asn Trp Lys Thr Leu Tyr Glu Val Lys Ser Glu
1               5                   10                  15

Asn Leu Gly Gln Gly Asp Lys Pro Asp Tyr Phe Ser Ser Val Ala Thr
            20                  25                  30

Val Val Tyr Leu Arg Lys Glu Asn Cys Met Tyr Gln Ala Cys Pro Thr
            35                  40                  45

Gln Asp Cys Asn Lys Lys Val Ile Asp Gln Gln Asn Gly Leu Tyr Arg
        50                  55                  60

Cys Glu Lys Cys Asp Thr Glu Phe Pro Asn Phe Lys Tyr Arg Met Ile
65                  70                  75                  80

Leu Ser Val Asn Ile Ala Asp Phe Gln Glu Asn Gln Trp Val Thr Cys
                85                  90                  95

Phe Gln Glu Ser Ala Glu Ala Ile Leu Gly Gln Asn Ala Ala Tyr Leu
            100                 105                 110

Gly Glu Leu Lys Asp Lys Asn Glu Gln Ala Phe Glu Glu Val Phe Gln
        115                 120                 125
```

-continued

Asn Ala Asn Phe Arg Ser Phe Ile Phe Arg Val Arg Val Lys Val Glu
    130                 135                 140

Thr Tyr Asn Asp Glu Ser Arg Ile Lys Ala Thr Val Met Asp Val Lys
145                 150                 155                 160

Pro Val Asp Tyr Arg Glu Tyr Gly Arg Arg Leu Val Met Ser Ile Arg
                165                 170                 175

Arg Ser Ala Leu Met
            180

<210> SEQ ID NO 12
<211> LENGTH: 543
<212> TYPE: DNA
<213> ORGANISM: Homo sapiens

<400> SEQUENCE: 12
ggagggagta acaccaactg gaaaaccttg tatgaggtca aatccgagaa cctgggccaa      60
ggcgacaagc cggactactt tagttctgtg gccacagtgg tgtatcttcg caaagagaac     120
tgcatgtacc aagcctgccc gactcaggac tgcaataaga aagtgattga tcaacagaat     180
ggattgtacc gctgtgagaa gtgcgacacc gaatttccca atttcaagta ccgcatgatc     240
ctgtcagtaa atattgcaga ttttcaagag aatcagtggg tgacttgttt ccaggagtct     300
gctgaagcta tccttggaca aaatgctgct tatcttgggg aattaaaaga caagaatgaa     360
caggcatttg aagaagtttt ccagaatgcc aacttccgat ctttcatatt cagagtcagg     420
gtcaaagtgg agacctacaa cgacgagtct cgaattaagg ccactgtgat ggacgtgaag     480
cccgtggact acagagagta tggccgaagg ctggtcatga gcatcaggag aagtgcattg     540
atg                                                                   543

<210> SEQ ID NO 13
<211> LENGTH: 198
<212> TYPE: PRT
<213> ORGANISM: Homo sapiens

<400> SEQUENCE: 13

Glu Ala Ser Pro Ala Ser Gly Pro Arg His Leu Met Asp Pro His Ile
1               5                   10                  15

Phe Thr Ser Asn Phe Asn Asn Gly Ile Gly Arg His Lys Thr Tyr Leu
                20                  25                  30

Cys Tyr Glu Val Glu Arg Leu Asp Asn Gly Thr Ser Val Lys Met Asp
            35                  40                  45

Gln His Arg Gly Phe Leu His Asn Gln Ala Lys Asn Leu Leu Cys Gly
        50                  55                  60

Phe Tyr Gly Arg His Ala Glu Leu Arg Phe Leu Asp Leu Val Pro Ser
65                  70                  75                  80

Leu Gln Leu Asp Pro Ala Gln Ile Tyr Arg Val Thr Trp Phe Ile Ser
                85                  90                  95

Trp Ser Pro Cys Phe Ser Trp Gly Cys Ala Gly Glu Val Arg Ala Phe
                100                 105                 110

Leu Gln Glu Asn Thr His Val Arg Leu Arg Ile Phe Ala Ala Arg Ile
        115                 120                 125

Tyr Asp Tyr Asp Pro Leu Tyr Lys Glu Ala Leu Gln Met Leu Arg Asp
    130                 135                 140

Ala Gly Ala Gln Val Ser Ile Met Thr Tyr Asp Glu Phe Lys His Cys
145                 150                 155                 160

Trp Asp Thr Phe Val Asp His Gln Gly Cys Pro Phe Gln Pro Trp Asp

-continued

```
                    165                 170                 175
Gly Leu Asp Glu His Ser Gln Ala Leu Ser Gly Arg Leu Arg Ala Ile
            180                 185                 190

Leu Gln Asn Gln Gly Asn
        195

<210> SEQ ID NO 14
<211> LENGTH: 594
<212> TYPE: DNA
<213> ORGANISM: Homo sapiens

<400> SEQUENCE: 14
gaggcatctc cagcaagcgg accaaggcac ctgatggacc cccacatctt cacctctaac      60
tttaacaatg gcatcggcag gcacaagaca tacctgtgct atgaggtgga gcgcctggac     120
aacggcacca gcgtgaagat ggatcagcac agaggcttcc tgcacaacca ggccaagaat     180
ctgctgtgcg gcttctacgg ccggcacgca gagctgagat ttctggacct ggtgcctagc     240
ctgcagctgg atccagccca gatctatagg gtgacctggt tcatcagctg gtccccatgc     300 tttttcctggg gatgtgcagg agaggtgcgc gccttcctgc aggagaatac acacgtgcgg     360
ctgagaatct tgccgcccg gatctacgac tatgatcctc tgtacaagga ggccctgcag     420
atgctgagag acgcaggagc ccaggtgtcc atcatgacct atgatgagtt caagcactgc     480
tgggacacat ttgtggatca ccagggctgt ccctttcagc cttgggacgg actggatgag     540
cactcccagg ccctgtctgg caggctgagg gccatcctgc agaaccaggg caat          594

<210> SEQ ID NO 15
<211> LENGTH: 198
<212> TYPE: PRT
<213> ORGANISM: Homo sapiens

<400> SEQUENCE: 15

Glu Ala Ser Pro Ala Ser Gly Pro Arg His Leu Met Asp Pro His Ile
1               5                   10                  15

Phe Thr Ser Asn Phe Asn Asn Gly Ile Gly Arg His Lys Thr Tyr Leu
            20                  25                  30

Cys Tyr Glu Val Glu Arg Leu Asp Asn Gly Thr Ser Val Lys Met Asp
        35                  40                  45

Gln His Arg Gly Phe Leu His Gly Gln Ala Lys Asn Leu Leu Cys Gly
    50                  55                  60

Phe Tyr Gly Arg His Ala Glu Leu Arg Phe Leu Asp Leu Val Pro Ser
65                  70                  75                  80

Leu Gln Leu Asp Pro Ala Gln Ile Tyr Arg Val Thr Trp Phe Ile Ser
            85                  90                  95

Trp Ser Pro Cys Phe Ser Trp Gly Cys Ala Gly Glu Val Arg Ala Phe
            100                 105                 110

Leu Gln Glu Asn Thr His Val Arg Leu Arg Ile Phe Ala Ala Arg Ile
        115                 120                 125

Tyr Asp Tyr Asp Pro Leu Tyr Lys Glu Ala Leu Gln Met Leu Arg Asp
    130                 135                 140

Ala Gly Ala Gln Val Ser Ile Met Thr Tyr Asp Glu Phe Lys His Cys
145                 150                 155                 160

Trp Asp Thr Phe Val Asp His Gln Gly Cys Pro Phe Gln Pro Trp Asp
            165                 170                 175

Gly Leu Asp Glu His Ser Gln Ala Leu Ser Gly Arg Leu Arg Ala Ile
            180                 185                 190
```

Leu Gln Asn Gln Gly Asn
        195

<210> SEQ ID NO 16
<211> LENGTH: 594
<212> TYPE: DNA
<213> ORGANISM: Homo sapiens

<400> SEQUENCE: 16
gaggcatctc cagcaagcgg accaaggcac ctgatggacc cccacatctt cacctctaac        60
tttaacaatg gcatcggcag gcacaagaca tacctgtgct atgaggtgga gcgcctggac       120
aacggcacca gcgtgaagat ggatcagcac agaggcttcc tgcacggcca ggccaagaat       180
ctgctgtgcg gcttctacgg ccggcacgca gagctgagat ttctggacct ggtgcctagc       240
ctgcagctgg atccagccca gatctatagg gtgacctggt tcatcagctg gtccccatgc       300
ttttcctggg gatgtgcagg agaggtgcgc gccttcctgc aggagaatac acacgtgcgg       360
ctgagaatct ttgccgcccg gatctacgac tatgatcctc tgtacaagga ggccctgcag       420
atgctgagag acgcaggagc ccaggtgtcc atcatgacct atgatgagtt caagcactgc       480
tgggacacat ttgtggatca ccagggctgt cccttttcagc cttgggacgg actggatgag       540
cactcccagg ccctgtctgg caggctgagg gccatcctgc agaaccaggg caat              594

<210> SEQ ID NO 17
<211> LENGTH: 23
<212> TYPE: DNA
<213> ORGANISM: Homo sapiens

<400> SEQUENCE: 17
gagtccgagc agaagaagaa ggg                                                23

<210> SEQ ID NO 18
<211> LENGTH: 23
<212> TYPE: DNA
<213> ORGANISM: Homo sapiens

<400> SEQUENCE: 18 ttctacacccc cagccgcccc agg                                               23

<210> SEQ ID NO 19
<211> LENGTH: 23
<212> TYPE: DNA
<213> ORGANISM: Homo sapiens

<400> SEQUENCE: 19 gacccccctcc accccgcctc cgg                                               23

<210> SEQ ID NO 20
<211> LENGTH: 23
<212> TYPE: DNA
<213> ORGANISM: Homo sapiens

<400> SEQUENCE: 20
cgctacacgg tgctgagcgt ggg                                                23

<210> SEQ ID NO 21
<211> LENGTH: 23
<212> TYPE: DNA
<213> ORGANISM: Homo sapiens

<400> SEQUENCE: 21

-continued ggcccagact gagcacgtga tgg                                             23

<210> SEQ ID NO 22
<211> LENGTH: 23
<212> TYPE: DNA
<213> ORGANISM: Homo sapiens

<400> SEQUENCE: 22
ggcactgcgg ctggaggtgg ggg                                             23

<210> SEQ ID NO 23
<211> LENGTH: 23
<212> TYPE: DNA
<213> ORGANISM: Homo sapiens

<400> SEQUENCE: 23
gacatcgatg tcctccccat tgg                                             23

<210> SEQ ID NO 24
<211> LENGTH: 23
<212> TYPE: DNA
<213> ORGANISM: Homo sapiens

<400> SEQUENCE: 24
agggatcgtc tttcaaggcg agg                                             23

<210> SEQ ID NO 25
<211> LENGTH: 23
<212> TYPE: DNA
<213> ORGANISM: Homo sapiens

<400> SEQUENCE: 25
ggaatccctt ctgcagcacc tgg                                             23

<210> SEQ ID NO 26
<211> LENGTH: 23
<212> TYPE: DNA
<213> ORGANISM: Homo sapiens

<400> SEQUENCE: 26
gtgctgggct ccggtgcgtt cgg                                             23

<210> SEQ ID NO 27
<211> LENGTH: 23
<212> TYPE: DNA
<213> ORGANISM: Homo sapiens

<400> SEQUENCE: 27
caaagcagaa actcacatcg agg                                             23

<210> SEQ ID NO 28
<211> LENGTH: 23
<212> TYPE: DNA
<213> ORGANISM: Homo sapiens

<400> SEQUENCE: 28
ctccctcaag caggccccgc tgg                                             23

<210> SEQ ID NO 29
<211> LENGTH: 23
<212> TYPE: DNA
<213> ORGANISM: Homo sapiens -continued

```
<400> SEQUENCE: 29
gtgctgggct ccggtgcgtt cgg                                        23

<210> SEQ ID NO 30
<211> LENGTH: 23
<212> TYPE: DNA
<213> ORGANISM: Homo sapiens

<400> SEQUENCE: 30
ttctcggagg ctcaggtgcg tgg                                        23

<210> SEQ ID NO 31
<211> LENGTH: 23
<212> TYPE: DNA
<213> ORGANISM: Homo sapiens

<400> SEQUENCE: 31
gctcccatca catcaaccgg tgg                                        23

<210> SEQ ID NO 32
<211> LENGTH: 23
<212> TYPE: DNA
<213> ORGANISM: Homo sapiens

<400> SEQUENCE: 32
gccctctgtg tgctcaaggg ggg                                        23

<210> SEQ ID NO 33
<211> LENGTH: 23
<212> TYPE: DNA
<213> ORGANISM: Homo sapiens

<400> SEQUENCE: 33
catgcccttc ggctgcctcc tgg                                        23

<210> SEQ ID NO 34
<211> LENGTH: 23
<212> TYPE: DNA
<213> ORGANISM: Homo sapiens

<400> SEQUENCE: 34
taataattga tgtcatagat tgg                                        23

<210> SEQ ID NO 35
<211> LENGTH: 24
<212> TYPE: DNA
<213> ORGANISM: Homo sapiens

<400> SEQUENCE: 35
ggctattggt caaggcaagg ctgg                                       24

<210> SEQ ID NO 36
<211> LENGTH: 23
<212> TYPE: DNA
<213> ORGANISM: Mus musculus

<400> SEQUENCE: 36
acatctcatc aaggacttgt tgg                                        23
```

FUSION PROTEIN THAT IMPROVES GENE EDITING EFFICIENCY AND APPLICATION THEREOF

CROSS-REFERENCE TO RELATED APPLICATIONS

The present disclosure is a continuation-in-part of International Application No. PCT/CN2020/137239, filed on Dec. 17, 2020 which claims the benefit of Chinese Patent Application No. 201911310969.8, filed on Dec. 18, 2019, Chinese Patent Application No. 201911312544.0, filed on Dec. 18, 2019, and Chinese Patent Application No. 210911312537.0, filed on Dec. 18, 2019. The entire disclosures of the applications referenced above are incorporated herein by reference.

SEQUENCE LISTING

This application contains references to amino acid sequences and/or nucleic acid sequences which have been submitted concurrently herewith as the sequence listing text file entitled "[P22413504US].Sequence Listing.TXT", file size 34 KiloBytes (KB), created on Jun. 17, 2022. The aforementioned sequence listing is hereby incorporated by reference in its entirety pursuant to 37 C.F.R. § 1.52(e)(5).

FIELD

The present disclosure relates to the field of biotechnology, and in particular to a fusion protein that improves gene editing efficiency and application thereof.

BACKGROUND

Since 2013, a new generation of gene editing technology represented by CRISPR/Cas9 has entered various experiments in the field of biology, which changes the traditional means of gene manipulation. In April 2016, David Liu's laboratory firstly reported a single-base gene editing technology. Afterwards, other types of single-base gene editing technology based on a principle of cytosine deaminase (such as cytosine deaminase derived from lamprey and human being fused with dCas9 or Cas9n in different ways) were also reported successively. It uses spCas9 derived from *Streptococcus pyogenes* in CRISPR/Cas9, takes NGG as PAM (protospacer adjacent motif), and recognizes and specifically binds DNA, which realizes single-base mutation from C to T or G to A upstream of NGG.

The single-base gene editing technology has been reported to be highly effective in conducting gene mutation or repair of genomes, making animal models of disease and gene therapy. Currently, among the discovered single-base gene editing tools, BE3 (Base Editor 3) is the most widely applied. The BE3 has a base substitution efficiency of up to 37%, which is much higher than that achieved by homologous recombination, while maintaining a lower off-target effect, demonstrating its great potential in single-base mutation modification or single-base mutation therapy in the genome. With the deepening of the research, it has been found that the introduction two or more copies of UGI (uracil glycosidase inhibitor) into BE3 could further enhance the editing efficiency and product purity. With the introduction of bipartite NLS (nuclear localization signal) and codon (namely BE4max), the editing efficiency is further improved. These methods can improve the efficiency to some extent, but with relative limitations.

Beta-hemoglobinopathy, such as beta-thalassemia and sickle cell disease (SCD), are caused by mutations of the gene HBB that encodes beta-hemoglobin. In rare cases, hereditary persistence of fetal hemoglobin (HPFH) is a benign hereditary disease in which high expression of gamma-globin in adult patients can alleviate disease phenotypes resulting from mutations in beta-hemoglobin. It has been reported that the deletion of 13 bp of HBG1/2 promoter region with CRISPR/Cas9 can activate the expression of gamma-globulin, thus alleviate or treat thalassemia disease, which is an effective therapeutic strategy. It is reported that in one of the patients with HPFH, the heterozygous point mutation (G>A) at site −117 of HBG1/2 promoter region produces 10-20% expression of fetal hemoglobin (HbF), and its mechanism is that the mutation of −117 G>A destroys the binding site of transcription repressor BCL11A.

The efficiency of the existing gene editing technology using CRISPR/Cas9-mediated homologous recombination to prepare animal models due to base substitution is still relatively low. The novel single-base gene editing technology has attracted much attention for its 100% efficiency in producing the animal models of disease. However, the existing single-base gene editing technology is usually C3-C8, which is not very effective in targeting to C adjacent of the PAM region.

SUMMARY

Aiming at the defects existed in the prior art, an objective of the present disclosure is to provide a fusion protein that improves gene editing efficiency and application thereof.

In one aspect, the present disclosure provides a fusion protein for improving gene editing efficiency, which comprises functional domain of a single-stranded DNA binding protein, nucleoside deaminase and nuclease.

Specifically, the connection sequence of the fusion protein is as follows: the nucleoside deaminase is located at N-terminal or C-terminal of the nuclease, and the functional domain of the single-stranded DNA binding protein is located at the N-terminal or C-terminal of the nucleoside deaminase and the nuclease, and/or between the nucleoside deaminase and the nuclease;

preferably, the nucleoside deaminase is located at the N-terminal of the nuclease;

more preferably, the functional domain of the single-stranded DNA binding protein is located between the nucleoside deaminase and the nuclease.

In the fusion proteins described above, the single-stranded DNA binding protein comprises sequence-specific single-stranded DNA binding protein and/or non-sequence-specific single-stranded DNA binding protein, preferably, the non-sequence-specific single-stranded DNA binding protein;

preferably, the non-sequence specific single-stranded DNA binding protein is selected from one or more of RPA70 (subunit 70 of human replication protein A), RPA32 (subunit 32 of human replication protein A), BRCA2 (breast cancer gene 2), hnRNPK (heterogeneous nuclear ribonucleoprotein K), PUF60 (poly-U binding splicing factor 60 KDa) and Rad51 (a homologous recombination repair protein);

preferably, the sequence-specific single-stranded DNA binding protein is selected from one or more of TEBP (telomere binding protein), Teb1 (a constituent protein of telomerase) and POT1 (human shelterin protein 1);

preferably, the functional domain of the single-stranded DNA binding protein comprises at least one (any one, any two, any three or all four) of the following four domains, or partial polypeptide fragments of the following four domains having a function of binding to single-stranded DNA, and any combination thereof: OB fold (oligonucleotide/oligosaccharide/oligopeptide-binding fold), KH domain (K homologous domain), RRMS (RNA recognition motif) and whirly domains of the single-stranded DNA binding protein; more preferably, the functional domain of the single-stranded DNA binding protein comprises DNA binding domain (DBD) of Rad51, more preferably, amino acid sequence of the DNA binding domain of Rad51 comprises a sequence of SEQ ID NO: 1, more preferably, coding sequence of the DNA binding domain of Rad51 comprises a sequence of SEQ ID NO: 2;

more preferably, amino acid sequence of the DNA binding domain of RPA70 comprises a sequence of SEQ ID NO: 11, and more preferably, coding sequence of the DNA binding domain of RPA70 comprises a sequence of SEQ ID NO: 12.

In the fusion proteins described above, the deaminase comprises cytosine deaminase (APOBEC) and/or adenosine deaminase, preferably, the cytosine deaminase can be derived from different organisms;

in some embodiments, the cytosine deaminase comprises rat-derived cytosine deaminase, preferably, amino acid sequence of the rat-derived cytosine deaminase comprises a sequence of SEQ ID NO: 3, more preferably, coding sequence of the rat-derived cytosine deaminase comprises a sequence of SEQ ID NO: 4;

in some embodiments, the cytosine deaminase comprises human-derived cytosine deaminase APOBEC3A, preferably, amino acid sequence of the human-derived cytosine deaminase APOBEC3A comprises a sequence of SEQ ID NO: 13, more preferably, coding sequence of the cytosine deaminase APOBEC3A comprises a sequence of SEQ ID NO: 14;

in some embodiments, the cytosine deaminase comprises a mutant of the cytosine deaminase APOBEC3A, the mutant of the cytosine deaminase APOBEC3A mutates asparagine (N or Asn) at position 57 (from initiation codon) of the cytosine deaminase APOBEC3A to glycine (G or Gly), preferably, the cytosine deaminase APOBEC3A is derived from human, more preferably, amino acid sequence of the cytosine deaminase APOBEC3A comprises the sequence of SEQ ID NO: 13, and more preferably, coding sequence of the cytosine deaminase APOBEC3A comprises the sequence of SEQ ID NO: 14; and amino acid sequence of the mutant of the cytosine deaminase APOBEC3A comprises a sequence of SEQ ID NO: 15, and more preferably, coding sequence of the cytosine deaminase APOBEC3A comprises a sequence of SEQ ID NO: 16;

in the fusion proteins described above, the nuclease is selected from one or more of Cas9, Cas3, Cas8a, Cas8b, Cas10d, Cse1, Csy1, Csn2, Cas4, Cas10, Csm2, Cmr5, Fok1 and Cpf1; preferably, the nuclease is Cas9; more preferably, the Cas9 is selected from Cas9 derived from *Streptococcus pneumoniae, Staphylococcus aureus, Streptococcus pyogenes* or *Streptococcus thermophilus*; more preferably, the Cas9 is selected from Cas9 mutants VQR-spCas9, VRER-spCas9, and spCas9n; more preferably, spCas9n, and more preferably, amino acid sequence of spCas9n comprises a sequence of SEQ ID NO: 5; and more preferably, coding sequence of spCas9n comprises a sequence of SEQ ID NO: 6.

In the fusion proteins described above, NLS (nuclear localization signal) is further comprised; preferably, the NLS is located at at least one terminal (C-terminal and/or N-terminal) of the fusion protein; more preferably, amino acid sequence of the NLS comprises a sequence of SEQ ID NO: 7, and more preferably, coding sequence of the NLS comprises a sequence of SEQ ID NO: 8;

the fusion protein further comprises UGI (uracil glycosidase inhibitor), preferably, the UGI is located at at least one terminal (C-terminal and/or N-terminal) of the fusion protein; more preferably, amino acid sequence of the UGI comprises a sequence of SEQ ID NO: 9; more preferably, coding sequence of UGI comprises a sequence of SEQ ID NO: 10; and more preferably, the UGI has more than two copies.

In another aspect, the present disclosure also provides any one of the following A)-C) biomaterials:

A) a gene encoding any one of the fusion proteins described above; wherein the gene is DNA or RNA (such as mRNA);

B) a recombinant vector comprising the gene of A); wherein the recombinant vector comprises a viral vector and/or a non-viral vector; the viral vector comprises adeno-associated viral vector, adenoviral vector, lentiviral vector, retroviral vector and/or oncolytic virus vector; and the non-viral vector comprises cationic high-molecular polymer, plasmid vector and/or liposome;

C) a recombinant cell or recombinant bacterium containing any one of the fusion proteins described above or the gene of A), wherein the recombinant bacterium can be engineered bacteria, and the recombinant cell can be target cells to be edited, such as immune cells (such as T cells), hematopoietic stem cells, bone marrow cells, red blood cells, preferably, red blood cell precursor cells or hematopoietic stem cells.

In another aspect, the present disclosure also provides an sgRNA for gene editing of target gene in cells, wherein target sequence of the sgRNA comprises at least one of SEQ ID NO: 17-36, preferably, the cells are T cells, hematopoietic stem cells, bone marrow cells or red blood cells, more preferably, red blood cell precursor cells or hematopoietic stem cells.

preferably, the target gene is at the promotor of HBG1 or HB G2 (specifically, G at site −117 is edited as A, and the G at site −117 is the G at position 14 from the left in the promoter region CCAGCCTTGCCTTGAC-CAATAGCC).

In another aspect, the present disclosure also provides a single-base gene editing system, which comprises any one of the fusion proteins described above or the biomaterials and the sgRNA, wherein the sgRNA guides the fusion protein to conduct single-base gene editing on the target gene in the target cell;

preferably, the target sequence of the sgRNA comprises at least one of SEQ ID NO: 17-36;

and/or, the cells are T cells, hematopoietic stem cells, bone marrow cells, red blood cells or red blood cell precursor cells, and/or, the target gene is at the promoter of HBG1 or HBG2.

In another aspect, the present disclosure claims use of any one of the fusion proteins described above, the biomaterials and the single-base gene editing system in preparing a product for gene editing, treating and/or preventing disease, animal model or a new plant variety;

in some embodiments, the disease is beta-hemoglobin-opathy, wherein the beta-hemoglobinopathy comprises beta-thalassemia and/or sickle cell anemia.

In another aspect, the present disclosure also provides a method for improving the efficiency of single-base gene editing, which comprises the steps of introduction any one of the fusion proteins described above and the sgRNA into a cell and conducting the gene-editing on the target gene, wherein the sgRNA guides the fusion protein to conduct the single-base gene editing on the target gene.

In the method described above, preferably, the target sequence of the sgRNA comprises at least one of SEQ ID NO: 17-36;

and/or, the cells are T cells, hematopoietic stem cells, bone marrow cells, red blood cells or red blood cell precursor cells;

and/or, the target gene is at the promoter of HBG1 or HBG2.

In another aspect, the present disclosure also provides a method for constructing animal models of disease, which comprises the steps of introduction any one of the fusion proteins described above and the sgRNA into animal cells and conducting gene-editing on the target gene;

preferably, the target sequence of the sgRNA comprises at least one of SEQ ID NO: 17-36; more preferably, the target sequence of the sgRNA comprises the sequence of SEQ ID NO: 36; and the target gene comprises a DMD gene;

preferably, the animals are mammals; more preferably, the mammals are rats or mice, more preferably mice;

preferably, the cells are embryonic cells;

preferably, the method of introduction is one or any combination of vector transformation, microinjection, transfection, lipid transfection, heat shock, electropo-ration, transduction, gene gun, and DEAE-dextran mediated transfer, more preferably, microinjection;

preferably, the introduction is carried out using mRNA of any one of the above fusion proteins and the sgRNA, more preferably, the concentration of the mRNA of any one of the above fusion proteins used for the introduc-tion is 1-1,000 ng/μL, more preferably, 10-600 ng/μL, more preferably, 50-150 ng/μL, and more preferably, 100 ng/μL; and the concentration of the sgRNA used for the introduction is 1-1,000 ng/μL, more preferably, 10-600 ng/μL, more preferably, 150-250 ng/μL, and more preferably, 200 ng/μL, more preferably, the concentration ratio of the mRNA of any one of the above fusion proteins used for the introduction to the sgRNA used for the introduction is 1:(5-1), more preferably, 1:(4-1.5), more preferably, 1:(3-1.8), and more preferably, 1:2.

The present disclosure claims use of the animal model obtained by the method in drug screening, evaluation of the therapeutic effects of disease or research on treatment mechanism of diseases.

In another aspect, the present disclosure provides a prod-uct for treating and/or preventing beta-hemoglobinopathy, which comprises: a delivery vector of the gene described above in A) and the sgRNA.

The sgRNA guides the fusion protein to conduct single-base gene editing on the HBG1 and HBG2 promoter regions (specifically, the G at the site −117 is edited as A, and the G at the site −117 is the G at the position 14 from the left in the promoter region CCAGCCTTGCCTTGAC-CAATAGCC) in the target cell;

preferably, the target sequence of the sgRNA comprises the sequence of SEQ ID NO: 35;

preferably, the beta-hemoglobinopathy comprises beta-thalassemia and/or sickle cell anemia.

preferably, the cells are T cells, hematopoietic stem cells, bone marrow cells or red blood cells, and more pref-erably, red blood cell precursor cells or hematopoietic stem cells, preferably, the target gene is at the promotor of HBG1 or HBG2 (specifically, the G at the site −117 is edited as A, and the G at the site −117 is the G at the position 14 from the left in the promoter region CCAGCCTTGCCTTGACCAATAGCC).

In the above products, the delivery vector comprises a viral vector and/or a non-viral vector; the viral vector comprises adeno-associated viral vector, adenoviral vector, lentiviral vector, retroviral vector and/or oncolytic virus vector; and the non-viral vector comprises cationic high-molecular polymer, plasmid vector and/or liposome;

preferably, the delivery vector comprises lentiviral vector.

The term "at least one" described above refers to any one, any two combinations, any three combinations, . . . , or all combinations of all types defined therein, which are within the protection scope of the present application.

Among the above amino acid sequences or coding sequences, the sequences having more than 80%, more than 85%, more than 90%, more than 95%, more than 96%, more than 97%, more than 98%, or more than 99% homology with the sequences described in the present application, and/or the sequences subjected to substitution, deletion or insertion of amino acid residues or nucleotides based on the sequences described in the present application, and the sequences having the same or similar functions as that of the sequences used in the present application, are all within the protection scope of the present application.

The beneficial effects of the present disclosure are as follows:

In the present disclosure, in the process of conducting C-G to T-A base conversion according to CBEs (pyrimidine-base conversion technology), the nucleoside deaminase, such as cytosine deaminase, takes the single-stranded DNA as a substrate for deamination, and the fusion protein of the nucleoside deaminase and the nuclease is fused with the functional domain of the single-stranded DNA binding pro-tein, which greatly increases the chance of the single-stranded DNA being exposed to the nucleoside deaminase, thereby the base editing efficiency is obviously improved.

In the present disclosure, by screening the functional domains of 10 non-sequence-biased single-stranded DNA binding proteins for fusion with BE4max, it is found that a single-stranded DNA binding functional domain (1-114AA) derived from human Rad51 fused between Apobec1 and Cas9n shows the highest efficiency improvement, and is named as hyBE4max. Compared with BE4max, the C-G to T-A editing efficiency of the hyBE4max is improved up to 16 times, especially the efficiency at the site near the PAM region is improved more obviously, while maintaining lower indels (insertions or deletions).

The present disclosure makes a breakthrough improve-ment on the single-base gene editing technology, and can greatly promote its application in gene editing, gene therapy, cell therapy, animal model making, crop genetics and breed-ing, and the like aspects.

In gene therapy, the present disclosure takes beta-hemo-globinopathy as examples, as compared with eA3A-BE4max and A3A-BE4max, hyeA3A-BE4max targets the HBG1 and HBG2 promoter regions (hereinafter referred to as HBG1/2) closer to the site −117 of the PAM region, which can more accurately and efficiently target −117 to generate G-to-A mutation, thus activating the expression of gamma-globin, and providing a more accurate and efficient therapeutic strategy for beta-hemoglobinopathy.

The present disclosure applies hyA3A-BE4max to the making of mouse disease animal models. Compared with A3A-BE4max, hyA3A-BE4max is more effective in the generation of the disease animal models by targeting C-to-T mutations closer to the PAM region, thus the present disclosure provides a novel platform for making the disease animal models with high efficiency, which will greatly facilitate the production progress of different animal models.

BRIEF DESCRIPTION OF THE DRAWINGS

FIG. 7 shows the comparison of average C-to-T base editing efficiency (i.e., ordinate, in %) achieved by hyA3A-BE4max and A3A-BE4max at 8 endogenous targets on 293T.

FIG. 8 shows the comparison of base editing efficiency (i.e., ordinate, in %) of indels generated by hyA3A-BE4max and A3A-BE4max at 8 endogenous targets on 293T.

FIG. 9 shows a structural diagram of fusion proteins eA3A-BE4max and hyeA3A-BE4max. Wherein A3A N57G is an N57G mutant of hA3A used in FIG. 5 (its amino acid sequence is SEQ ID NO: 15 and coding sequence is SEQ ID NO: 16); and NLS, spCas9n and UGI are the same as those in FIG. 1.

Wherein C in the abscissa of FIGS. 2, 3, 5, 6, and 11 and the numbers following it represent the position of C edited as T on the corresponding target sequence, for example, C5 represents the efficiency of editing the C at position 5 from the 5' end of the corresponding target sequence as T.

Figure 13:
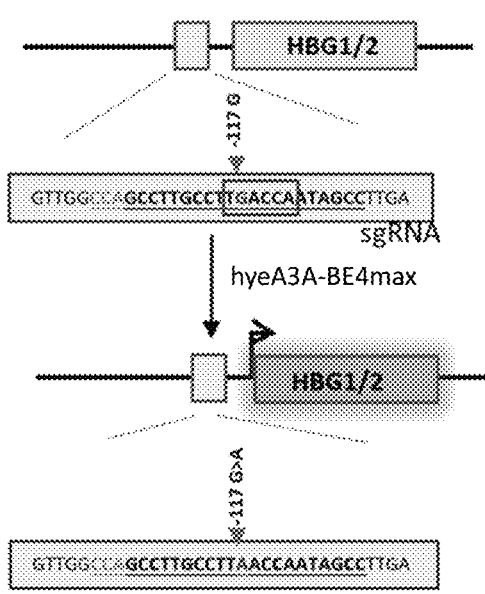

FIG. 13 shows a schematic diagram of hyeA3A-BE4max targeting HBG1/2 promoter region −117G, wherein −117 G>A mutation is shown in red, the core sequence of binding site of transcription factor BCL11A is indicated by a box, the PAM sequence is in blue, and G>A transformation destroys the binding site of transcription inhibitor BCL11A and activates the expression of HBG1/2 in HUDEP-2($\Delta^G\gamma$).

Figure 14:
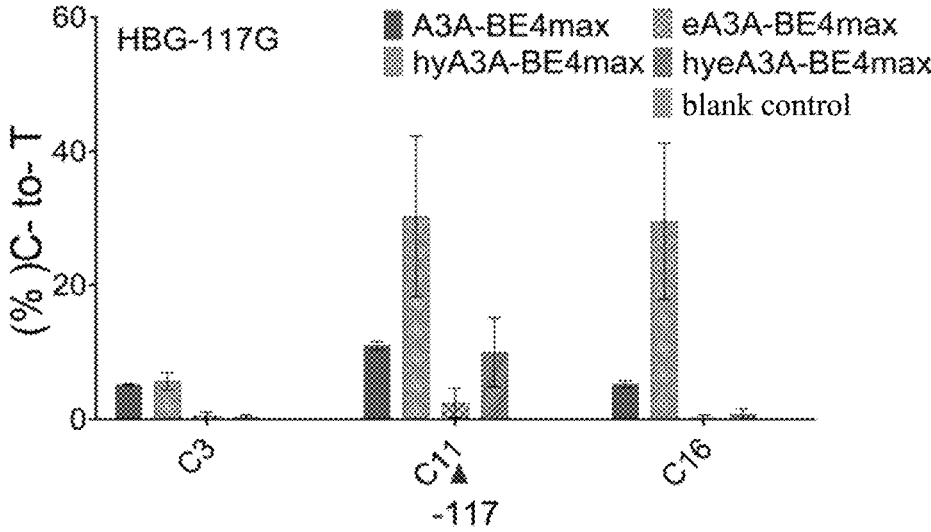

FIG. 14 shows the comparison of C-to-T base editing efficiency (i.e., ordinate, in %) achieved by hyeA3A-BE4max, eA3A-BE4max, A3A-BE4max, and hyA3A-BE4max targeting HBG-117G in HEK293T cells.

Figure 15:

FIG. 15 shows a schematic diagram of construction of lentiviral vectors Lenti-117G-hyA3A-BE4max-P2A-GFP and Lenti-117G-hyeA3A-BE4max-P2A-GFP. Wherein, the target sequence of the sgRNA is HBG-117G.

Figure 16:
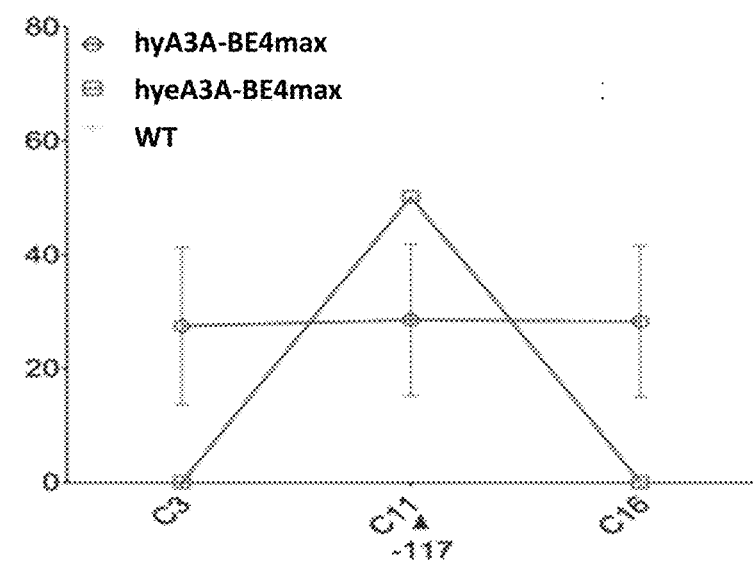

FIG. 16 shows the comparison of C-to-T base editing efficiency (i.e., ordinate, in %) achieved by hyeA3A-BE4max and hyA3A-BE4max targeting HBG-117G in HUDEP-2 ($\Delta^G\gamma$) cells.

Figure 17:
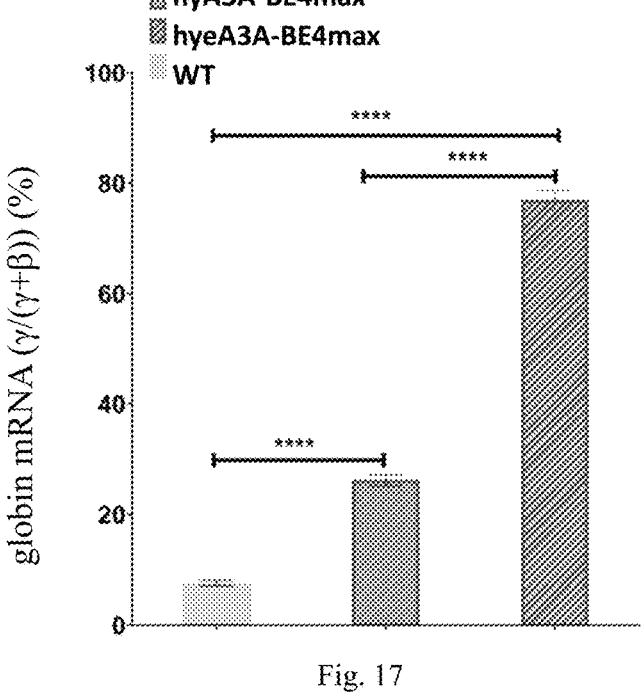

FIG. 17 shows the comparison of globin mRNA expression in HUDEP-2 ($\Delta^G\gamma$) cells infected with lentiviruses Lenti-117G-hyeA3A-BE4max-P2A-GFP and Lenti-117G-hyA3A-BE4max-P2A-GFP after cell differentiation. Wherein **** represents the difference significance level P<0.0001.

Figure 18:
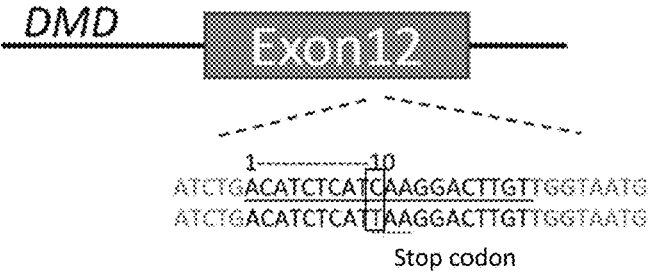

FIG. 18 shows a schematic diagram of animal model construction of hyA3A-BE4max targeting Duchenne muscular dystrophy (DMD) gene.

FIG. 19 shows the comparison of F0 high-throughput sequencing results after microinjection of A3A-BE4max and hyA3A-BE4max.

Figure 20:
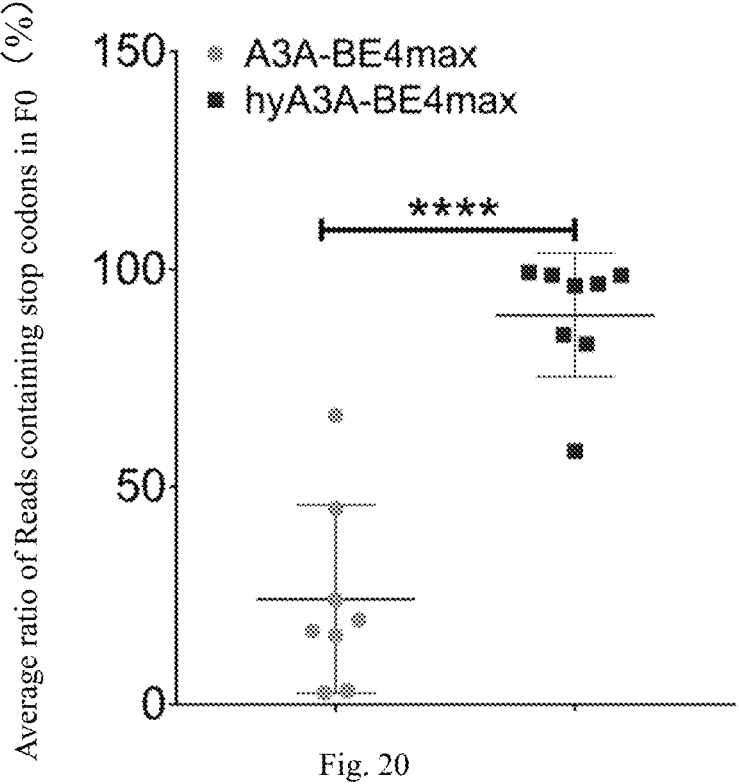

FIG. 20 shows the average ratio of Reads containing TAA stop codons in F0 produced by injection of A3A-BE4max and hyA3A-BE4max.

Figure 21:
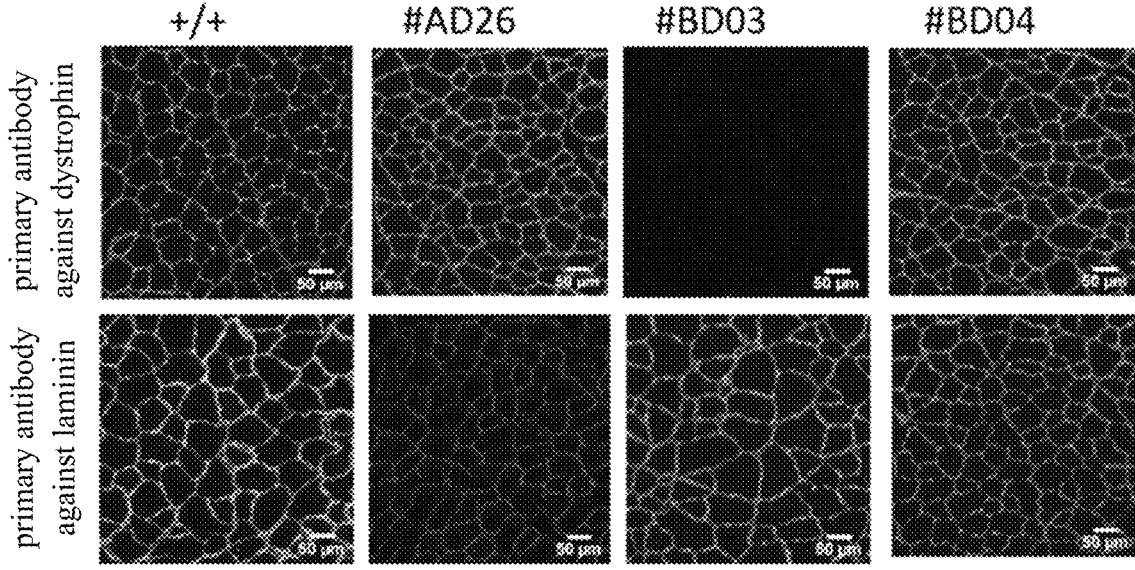

FIG. 21 shows the expression of dystrophin in F0 mice detected by immunofluorescence staining.

Figure 22:
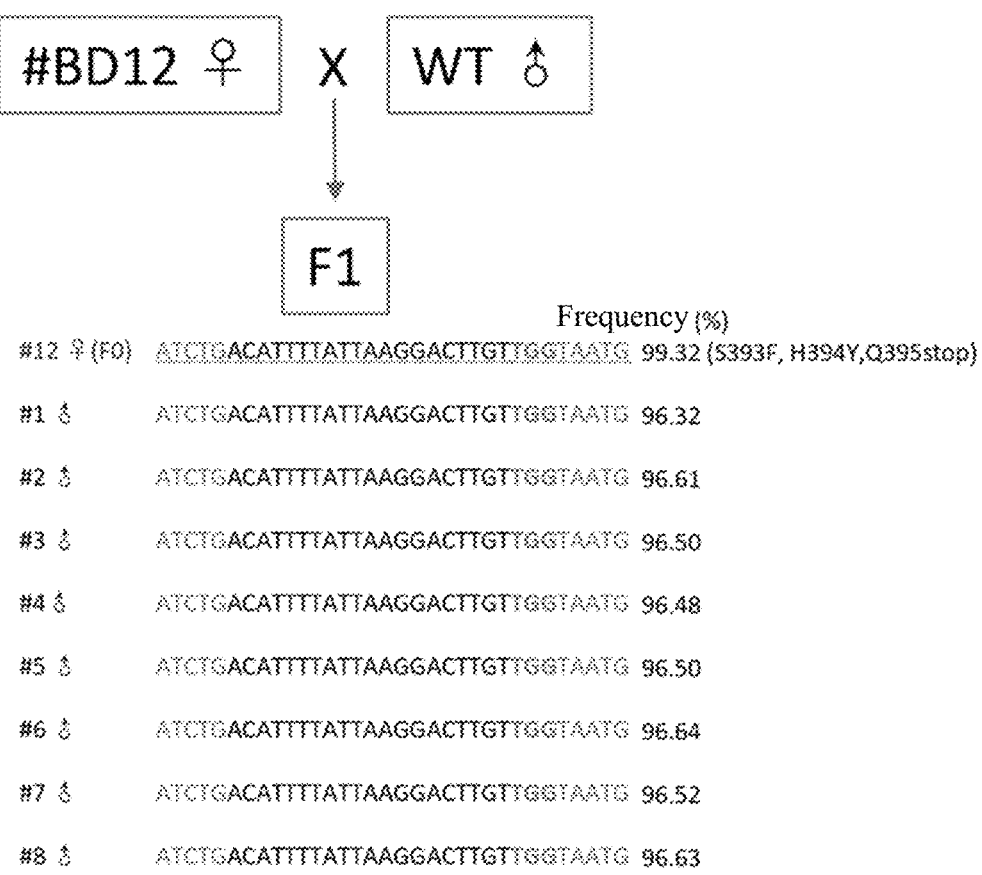

FIG. 22 shows the germ line inheritance (F0→F1) of DMD mutant mice.

Figure 23:
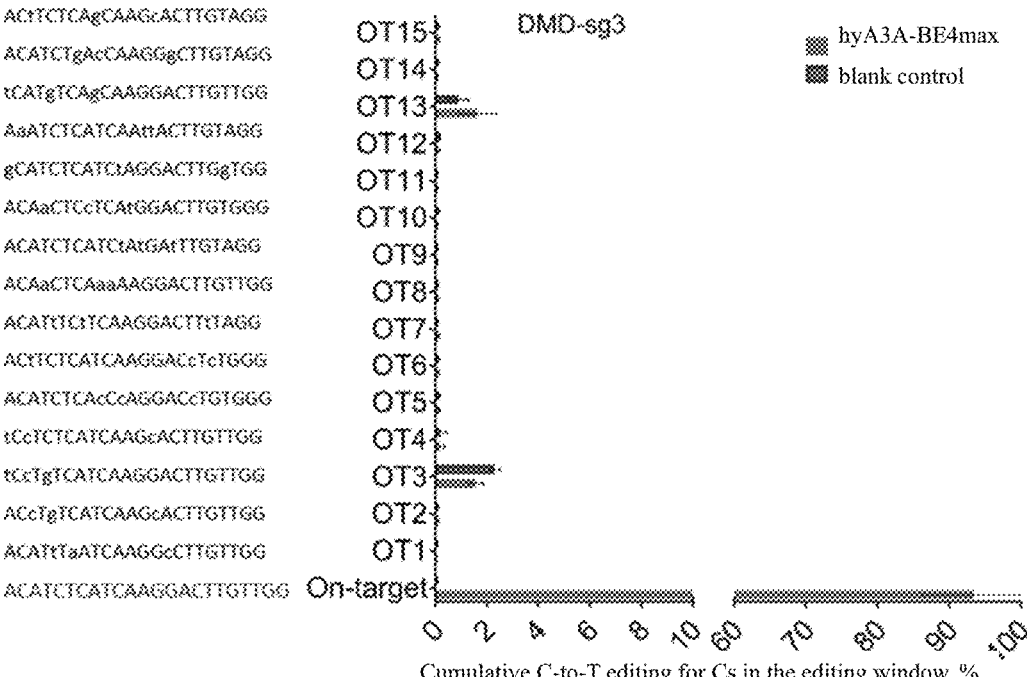

FIG. 23 shows the off-target analysis of the predicted off-target site combination of hyA3A-BE4max and DMD-sg3 on the F0 generation.

DETAILED DESCRIPTION 1. the Editing Efficiency of BE4Max Fused with the Functional Domain of Rad51DBD (1-114Aa) Single-Stranded DNA Binding Protein is Improved Most Obviously
1.1 Plasmid Design and Construction 1.1.1 According to the characteristics that Apobec1 of CBEs in single-base editing technology uses single-stranded DNA as substrate, we designed 10 different functional domains of human-derived non-sequence-biased single-stranded DNA binding proteins (mainly RPA70 (630aa)-A, RPA70-B, RPA70-AB, RPA70-C, RPA32-D, BRCA2-OB2, BRCA2-OB3, HNRNPK KH domain, PUF60 RRM, Rad51 DBD) (Table 1); since the reported fusion protein tended to be inactive at the C-terminal of BE4max (the first figure from top to bottom in FIG. 1), these functional domains were thus fused at the N-terminal of BE4max (the second figure from top to bottom in FIG. 1), and meanwhile, two endogenous targets EMX1 site1 and Tim3-sg1 from human were designed (the sequences are shown in Table 2).

1.1.2 DNAs of 10 different functional domains of human-derived non-sequence-biased single-stranded DNA binding proteins shown in Table 1 were synthesized, and then seamlessly cloned and assembled to the N-terminal of BE4max in plasmid pCMV-BE4max (addgene, #112093), and 10 recombinant plasmids were constructed respectively (FIG. 1): pRPA70-A-BE4max, pRPA70-B-BE4max, pRPA70-AB-BE4max, pRPA70-C-BE4max, pRPA32-D-BE4max, pBRCA2-OB2-BE4max, pBRCA2-OB3-BE4max, pKH-BE4max, pRRM-BE4max, and pRad51DBD-BE4max.

The DNAs of the targets EMX1 site1 and Tim3-sg1 shown in Table 2 were synthesized, and connected to Bbs I site of sgRNA expression plasmid U6-sgRNA-EF1α-GFP (used to express the sgRNA of the corresponding targets), respectively, to obtain recombinant plasmids pE and pT.

1.1.3 The plasmids constructed in 1.1.1 and 1.1.2 were sequenced by sanger to ensure that they are completely correct.

TABLE 1

Different functional domain sequences
of single-stranded DNA binding
proteins used

| Name | Sequence |
|---|---|
| RPA70-A | coding sequence (5'-3'): Cagtccaaagtggtgcccattgccagcctc actccttaccagtccaagtggaccatttgt gctcgtgttaccaacaaaagtcagatccgt acctggagcaactcccgaggggaagggaag cttttctccctagaactggttgacgaaagt ggtgaaatccgagctacagctttcaatgag caagtggacaagttctttcctcttattgaa gtgaacaaggtgtattatttctcgaaaggc accctgaagattgctaacaagcagttcaca gctgttaaaaatgactacgagatgaccttc aataacgagacttccgtcatgccctgtgag amino acid sequence: QSKVVPIASL TPYQSKWTICARVTNKSQIRTWSNSRGEGK LFSLELVDESGEIRATAFNEQVDKFFPLIE VNKVYYFSKGTLKIANKQFTAVKNDYEMTF NNETSVMPCE |
| RPA70-B | coding sequence (5'-3'): Gatttcacggggattgatgacctcgagaac aagtcgaaagactcacttgtagacatcatc gggatctgcaagagctatgaagacgccact aaaatcacagtgaggtctaacaacagagaa gttgccaagaggaatatctacttgatggac acatccgggaaggtggtgactgctacactg tgggggaagatgctgataaatttgatggt tctagacagcccgtgttggctatcaaagga gcccgagtctctgatttcggtggacggagc ctctccgtgctgtgtcttcaagcactatcatt gcgaatcctgacatcccagaggcctataag cttcgtggatggtttgacgcagaaggacaa gcctta amino acid sequence: DFTG IDDLENKSKDSLVDIIGICKSYEDATKITV RSNNREVAKRNIYLMDTSGKVVTATLWGED ADKFDGSRQPVLAIKGARVSDFGGRSLSVL SSSTIIANPDIPEAYKLRGWFDAEGQAL |
| RPA70-AB | encoding sequence (5'-3'): RPA 70-A + RPA70-B amino acid sequence: RPA70-A RPA70-B |

TABLE 1-continued

Different functional domain sequences
of single-stranded DNA binding
proteins used

| Name | Sequence |
|---|---|
| RPA70-C | coding sequence (5'-3'): Ggagggagtaacaccaactggaaaaccttg tatgaggtcaaatccgagaacctgggccaa ggcgacaagccggactactttagttctgtg gccacagtggtgtatcttcgcaaagagaac tgcatgtaccaagcctgcccgactcaggac tgcaataagaaagtgattgatcaacagaat ggattgtaccgctgtgagaagtgcgacacc gaatttcccaatttcaagtaccgcatgatc ctgtcagtaaatattgcagattttcaagag aatcagtgggtgacttgtttccaggagtct gctgaagctatccttggacaaaatgctgct tatcttggggaattaaaagacaagaatgaa caggcatttgaagaagttttccagaatgcc aacttccgatctttcatattcagagtcagg gtcaaagtggagacctacaacgacgagtct cgaattaaggccactgtgatggacgtgaag cccgtggactacagagagtatggccgaagg ctggtcatgagcatcaggagaagtgcattg atg (SEQ ID NO: 12) amino acid sequence: GGSNTNWKTLYEVKSENLGQGDKPDYFSSV ATVVYLRKENCMYQACPTQDCNKKVIDQQN GLYRCEKCDTEFPNFKYRMILSVNIADFQE NQWVTCFQESAEAILGQNAAYLGELKDKNE QAFEEVFQNANFRSFIFRVRVKVETYNDES RIKATVMDVKPVDYREYGRRLVMSIRRSAL M (SEQ ID NO: 11) |
| RPA32-D | coding sequence (5'-3'): Gcccagcacattgtgccctgtactatatct cagctgctttctgccactttggttgatgaa gtgttcagaattgggaatgttgagatttca caggtcactattgtggggatcatcagacat gcagagaaggctccaaccaacattgtttac aaaatagatgacatgacagctgcacccatg gacgttcgccagtgggttgacacagatgac accagcagtgaaaacactgtggttcctcca gaaacatatgtgaaagtggcaggccacctg agatcttttcagaacaaaaagagcctggta gcctttaagatcatgcccctggaggatatg aatgagttcaccacacatattctggaagtg atcaatgcacacatggtactaagcaaa amino acid sequence: AQHIVPCTISQLLSATLVDEVFRIGNVEIS QVTIVGIIRHAEKAPTNIVYKIDDMTAAPM DVRQWVDTDDTSSENTVVPPETYVKVAGHL RSFQNKKSLVAFKIMPLEDMNEFTTHILEV INAHMVLSK |
| BRCA2-OB2 | coding sequence (5'-3'): Ttatcatcgcttttcagtgatggaggaaat gttggttgtgttgatgtaattattcaaaga gcatacctatacagtggatggagaagaca tcatctggattatacatatttcgcaatgaa agagaggaagaaaaggaagcagcaaaatat gtggaggcccaacaaaagagactagaagcc ttattcactaaaattcaggaggaatttgaa gaacatgaagaaacacaacaaaccatat ttaccatcacgtgcactaacaagacagcaa gttcgtgctttgcaagatggtgcagagctt tatgaagcagtgaagaatgcagcagaccca gcttaccttgagggttatttcagtgaagag cagttaagagccttgaataatcacaggcaa atgttgaatgataagaaacaagctcagatc cagttggaaattaggaaggccatggaatct gctgaacaaaaggaacaaggttttatcaagg gatgtcacaaccgtgtggaagttgcgtatt gtaagctattcaaaaaaagaaaaagattca gttatactgagtatttggcgtccatcatca gatttatattctctgttaacagaaggaaag agatacagaatttatcatcttgcaacttca aaatctaaaagtaaatctgaaagagctaac |

TABLE 1-continued

Different functional domain sequences
of single-stranded DNA binding
proteins used

| Name | Sequence |
|---|---|
| | atacagttagcagcgacaaaaaaaactcag tatcaacaactaccggtttcagatgaaatt ttatttcagatttaccagccacgggagccc amino acid sequence: LSSLFSDGGNVGCVDVIIQRAYPIQWMEKT SSGLYIFRNEREEEKEAAKYVEAQQKRLEA LFTKIQEEFEEHEENTTKPYLPSRALTRQQ VRALQDGAELYEAVKNAADPAYLEGYFSEE QLRALNNHRQMLNDKKQAQIQLEIRKAMES AEQKEQGLSRDVTTVWKLRIVSYSKKEKDS VILSIWRPSSDLYSLLTEGKRYRIYHLATS KSKSKSERANIQLAATKKTQYQQLPVSDEI LFQIYQPREP |
| BRCA2-OB3 | coding sequence (5'-3'): Gacctaataggatttgtcgtttctgttgtg aaaaaaacaggacttgcccctttcgtctat ttgtcagacgaatgttacaatttactggca ataaagttttggatagaccttaatgaggac attattaagcctcatatgttaattgctgca agcaacctccagtggcgaccagaatccaaa tcaggccttcttactttatttgctggagat ttttctgtgtgttttctgctagtccaaaagag ggccactttcaagagacattcaacaaaatg aaaaatactgttgag amino acid sequence: DLIGFVVSVVKKTGLAPFVYLSDECYNLLA IKFWIDLNEDIIKPHMLIAASNLQWRPESK SGLLTLFAGDFSVFSASPKEGHFQETFNKM KNTVE |
| hnRNPK KH domain | coding sequence (5'-3'): Aacactgatgagatggttgaattacgcatt ctgcttcagagcaagaatgctggggcagtg attggaaaaggaggcaagaatattaaggct ctccgtacagactacaatgccagtgtttca gtcccagacagcagtggccccgagcgcata ttgagtatcagtgctgatattgaaacaatt ggagaaattctgaagaaaatcatccctacc ttggaagag amino acid sequence: NTDEMVELRILLQSKNAGAVIGKGGKNIKA LRTDYNASVSVPDSSGPERILSISADIETI GEILKKIIPTLEE |
| PUF60 RRM | coding sequence (5'-3'): Tgccgcgtctacgtgggctctatctactat gagctgggggaggacaccatccgccaggcc tttgccccctttggccccatcaagagcatc gacatgtcctgggactccgtcaccatgaag cacaagggctttgccttcgtggagtatgag gtccccgaagctgcacagctggccttggag cagatgaactcggtgatgctgggggggcagg aacatcaaggtgggcagacccagcaac amino acid sequence: CRVYVGSIYYELGEDTIRQAFAPFGPIKSI DMSWDSVTMKHKGFAFVEYEVPEAAQLALE QMNSVMLGGRNIKVGRPSN |
| Rad51 DBD | encoding sequence (5'-3'): Atggcaatgcagatgcagcttgaagcaaat gcagatacttcagtggaagaagaaagctttt ggcccacaacccatttcacggttagagcag tgtggcataaatgccaacgatgtgaagaaa ttggaagaagctggattccatactgtggag gctgttgcctatgcgccaaagaaggagcta ataaatattaagggaattagtgaagccaaa gctgataaaattctggctgaggcagctaaa ttagttccaatgggtttcaccactgcaact gaattccaccaaaggcggtcagagatcata cagattactactggctccaaagagcttgac aaactacttcaa (SEQ ID NO: 2) amino acid sequence: MAMQMQLEANADTSVEEESFGPQPISRLEQ |

TABLE 1-continued

Different functional domain sequences
of single-stranded DNA binding
proteins used

| Name | Sequence |
|---|---|
| | CGINANDVKKLEEAGFHTVEAVAYAPKKEL INIKGISEAKADKILAEAAKLVPMGFTTAT EFHQRRSEIIQITTGSKELDKLLQ (SEQ ID NO: 1) |

TABLE 2

Targets and sequences used

| Name of targets | Sequence (5'-3') | SEQ ID NO: |
|---|---|---|
| EMXI site1 | GAGTCCGAGCAGAAGAAGAAGGG | 17 |
| Tim3-sg1 | TTCTACACCCCAGCCGCCCCAGG | 18 |
| VEGFA site2 | GACCCCCTCCACCCCGCCTCCGG | 19 |
| Lag3-sg2 | CGCTACACGGTGCTGAGCGTGGG | 20 |
| HEK3 | GGCCCAGACTGAGCACGTGATGG | 21 |
| HEK4 | GGCACTGCGGCTGGAGGTGGGGG | 22 |
| EMX1-sg2p | GACATCGATGTCCTCCCCATTGG | 23 |
| Nme1-sg1 | AGGGATCGTCTTTCAAGGCGAGG | 24 |

1.2. Cell Transfection $5 \times 10^5$ HEK293T cells were plated into a 24-well plate. When the cells grew to 70%-80%, the plasmid combinations were transfected according to pssDBD-BE4max:pE (or pT)=750 ng:250 ng. 3 replicate wells were set for transfection of each plasmid combination, with $2 \times 10^5$ cells per well. Simultaneously, a blank control without transfection of any plasmid was set.

pssDBD-BE4max represents: any one of plasmids pRPA70-A-BE4max, pRPA70-B-BE4max, pRPA70-AB-BE4max, pRPA70-C-BE4max, pRPA32-D-BE4max, pBRCA2-OB2-BE4max, pBRCA2-OB3-BE4max, pKH-BE4max, pRRM-BE4max, and pRad51DBD-BE4max; and the plasmid pCMV-BE4max was used as a negative control.

1.3. Genome Extraction and Preparation of Amplicon Library.

72 h after transfection, genomic DNA of the cells was extracted using Tiangen Cell Genome Extraction Kit (DP304). Afterwards, the corresponding identification primers (Table 3) were designed according to the operation process of Hitom kit, i.e., a bridging sequence 5'-ggagt-gagtacggtgtgc-3' was added to the 5' terminal of the forward identification primer, and a bridging sequence 5'-gagttg-gatgctggatgg-3' was added to the 5' terminal of the reverse identification primer to obtain one round of PCR products; then, the first round of PCR products was used as a template to conduct a second round of PCR, followed by the PCR products were mixed together for gel-cutting, recovering, purification, and then sent to a company for deep sequencing.

TABLE 3

Identification primers of
the targets used

| Name of targets | Sequence (5'-3') |
|---|---|
| EMX1 site1 | F: ggagtgagtacggtgtgcGTGG TTCCAGAACCGGAGGACAAAG R: gagttggatgctggatggGTTT GTGGTTGCCCACCCTAGTCAT |
| Tim3-sg1 | F: ggagtgagtacggtgtgcCGCT TGAGTCTTGGCTCTCCTTCTC R: gagttggatgctggatggCACC ACGTTGCCACATTCAAACACA |
| VEGFA site2 | F: ggagtgagtacggtgtgcGACA GACAGACAGACACCGCCC R: gagttggatgctggatggACAG CCCAGAAGTTGGACGAAAAGT |
| Lag3-sg2 | F: ggagtgagtacggtgtgcTTCC TACCCCTGGAGCTTCTCAACT R: gagttggatgctggatggCCTC CGGGACCCACGCTCAG |
| HEK3 | F: ggagtgagtacggtgtgcAGGG AAACGCCCATGCAATTAGTCT R: gagttggatgctggatggCCCT GTCTAGGAAAAGCTGTCCTGC |
| HEK4 | F: ggagtgagtacggtgtgcCAGA GGGTCCAAAGCAGGATGACAG R: gagttggatgctggatggCTTT CAACCCGAACGGAGACACACA |
| EMX1-sg2p | F: ggagtgagtacggtgtgcGTGG TTCCAGAACCGGAGGACAAAG R: *gagttggatgctggatggGTTG TGGTTGCCCACCCTAGTCAT* |
| Nme1-sg1 | F: ggagtgagtacggtgtgcGGGG AGGCAGACACACAAACAGAAA R: gagttggatgctggatggGCGC TCATGACCTACCCTGTATCAC |

1.4. Analysis and Statistics of Deep Sequencing Results

The ratios of C to T and Indels were calculated by using the deep sequencing results of step 1.3 using a BE-analyzer website. The results were shown in Table 4 and Table 5.

The results show that, compared with BE4max, the BE4max fused with the functional domain of Rad51 single-stranded DNA binding protein (Rad51DBD-N-BE4max or Rad51DBD-BE4max) most obviously improved the C-to-T editing efficiency on the target, followed by the BE4max fused with the functional domain of a RPA70-C single-stranded DNA binding protein.

2. Best Editing Efficiency of hyBE4max

In order to further test the fusion position of the functional domain of Rad51 single-stranded DNA binding protein with the highest improvement on the C-to-T editing efficiency on the targets in step 1, the Rad51 DBD was fused to two other different positions of BE4max, and three recombinant plasmids of BE4max fused with Rad51 DBD (the third to the fifth figures from top to bottom in FIG. 1) were transfected into cells along with recombinant plasmids pE or pT, respectively, according to the method of 1.2 in step 1, and the results of editing efficiency were obtained according to the methods of 1.3 and 1.4 in step 1 (Table 4 and Table 5).

Figure 1:
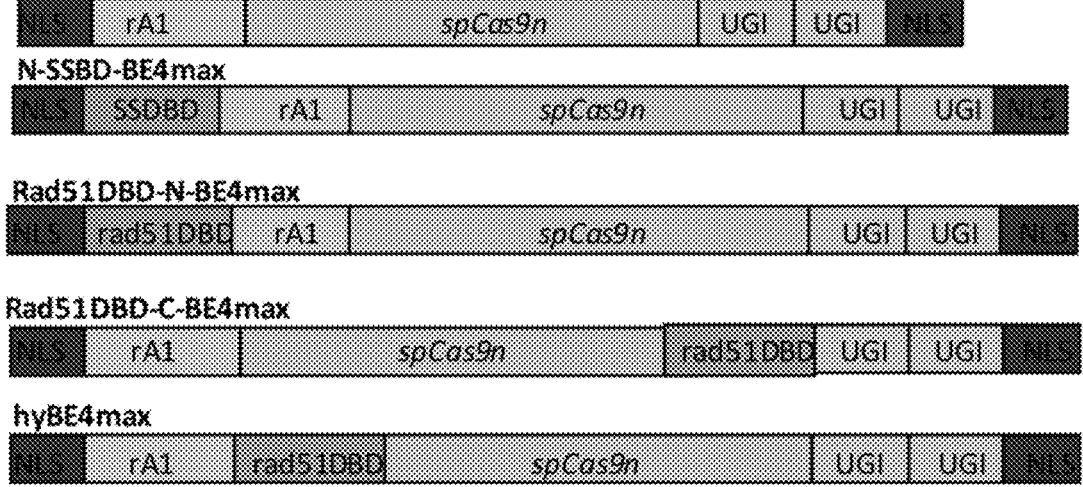
FIG. 1 shows a structural diagram of the fusion of the functional domains of different single-stranded DNA binding proteins with BE4max. Wherein NLS is a nuclear localization signal (its amino acid sequence is SEQ ID NO: 7 and coding sequence is SEQ ID NO: 8); rA1 is cytidine deaminase APOBEC1 (its amino acid sequence is SEQ ID NO: 3 and coding sequence is SEQ ID NO: 4); SpCas9n is a Cas9n derived from *Streptococcus pyogenes* (its amino acid sequence is SEQ ID NO: 5 and coding sequence is SEQ ID NO: 6); UGI is a uracil glycosidase inhibitor (its amino acid sequence is SEQ ID NO: 9 and coding sequence is SEQ ID NO: 10); and SSDBD is the functional domain of a single-stranded DNA binding protein.

Three types of BE4max fused with Rad51 DBD shown in the third to the fifth figures from top to bottom in FIG. 1 are as follows:

Rad51DBD-N-BE4max: Rad51 DBD was fused between NLS and rA1 in BE4max, i.e., Rad51 DBD was located at the N-terminal of rA1 and spCas9n;

Rad51DBD-C-BE4max: Rad51 DBD was fused between spCas9n and UGI in BE4max, i.e., Rad51 DBD was located at the C-terminal of rA1 and spCas9n;

hyBE4max: Rad51 DBD was fused between rA1 and spCas9n in BE4max.

TABLE 4

Results of editing efficiency of target
EMX1 site1 (in %)

| Base editor | Repeat | C5 | C6 |
|---|---|---|---|
| BE4max | Rep. 1 | 46.7 | 45.2 |
| | Rep. 2 | 44.9 | 42.9 |
| | Rep. 3 | 62.5 | 60.7 |
| RPA70-A-BE4max | Rep. 1 | 41 | 36.9 |
| | Rep. 2 | 41 | 36.9 |
| | Rep. 3 | 41.9 | 37.2 |
| RPA70-B-BE4max | Rep. 1 | 42.7 | 36.2 |
| | Rep. 2 | 42.6 | 36.3 |
| | Rep. 3 | 41 | 33.3 |
| RPA70-AB-BE4max | Rep. 1 | 48.4 | 47 |
| | Rep. 2 | 47.1 | 45.5 |
| | Rep. 3 | 45.7 | 44.1 |
| RPA70-C-BE4max | Rep. 1 | 65.2 | 63 |
| | Rep. 2 | 64.9 | 62.8 |
| | Rep. 3 | 64.7 | 62 |
| RPA32-D-BE4max | Rep. 1 | 41.8 | 37.3 |
| | Rep. 2 | 41.3 | 36.9 |
| | Rep. 3 | 41 | 36.7 |
| BRCA2-OB2-BE4max | Rep. 1 | 30 | 20.6 |
| | Rep. 2 | 30 | 20.5 |
| | Rep. 3 | 31 | 20.8 |
| BRCA2-OB3-BE4max | Rep. 1 | 32.5 | 25.8 |
| | Rep. 2 | 32.4 | 25.8 |
| | Rep. 3 | 32.1 | 25 |
| KH-BE4max | Rep. 1 | 34.8 | 21.7 |
| | Rep. 2 | 34.6 | 21.6 |
| | Rep. 3 | 31.9 | 19.3 |
| RRM-BE4max | Rep. 1 | 34.8 | 25.2 |
| | Rep. 2 | 35.2 | 25.3 |
| | Rep. 3 | 34.7 | 24.3 |
| Rad51DBD-BE4max | Rep. 1 | 68 | 66.4 |
| | Rep. 2 | 67.7 | 66.2 |
| | Rep. 3 | 65.9 | 60.6 |
| hyBE4max | Rep. 1 | 80.8 | 75.1 |
| | Rep. 2 | 81.3 | 75.5 |
| | Rep. 3 | 70 | 64.5 |
| BE4max-C-Rad51 | Rep. 1 | 41.5 | 38.9 |
| | Rep. 2 | 42.3 | 39.8 |
| | Rep. 3 | 45.2 | 42.9 |
| Blank control | Rep. 1 | 0.1 | 0 |
| | Rep. 2 | 0 | 0 |
| | Rep. 3 | 0 | 0 |

TABLE 5

Results of editing efficiency of target Tim3-sg1 (in %)

| Base editor | Repeat | C3 | C6 | C8 | C9 | C10 | C11 |
|---|---|---|---|---|---|---|---|
| BE4max | Rep. 1 | 24.1 | 25.2 | 21.3 | 17.9 | 5.6 | 2.5 |
| | Rep. 2 | 23.7 | 24.7 | 20.8 | 17.4 | 5.6 | 2.5 |
| | Rep. 3 | 24.3 | 25.9 | 21.4 | 17.9 | 5.2 | 2.5 |
| RPA72-A-BE4max | Rep. 1 | 17.7 | 17.7 | 11.9 | 10.5 | 7.1 | 4.7 |
| | Rep. 2 | 18 | 17.8 | 12 | 10.6 | 7.3 | 4.8 |
| | Rep. 3 | 17.9 | 17.6 | 12.3 | 10.7 | 7.5 | 5 |
| RPA72-B-BE4max | Rep. 1 | 15.4 | 14.2 | 9.9 | 8.3 | 5 | 2.9 |
| | Rep. 2 | 15.9 | 14.6 | 10.1 | 8.6 | 5.1 | 2.9 |
| | Rep. 3 | 15.1 | 14.3 | 9.4 | 7.8 | 4.7 | 2.7 |
| RPA72-AB-BE4max | Rep. 1 | 17.2 | 11.7 | 5.8 | 3.7 | 1.4 | 0.7 |
| | Rep. 2 | 17.3 | 11.6 | 5.8 | 3.7 | 1.4 | 0.6 |
| | Rep. 3 | 16.6 | 9.8 | 4.3 | 2.6 | 0.9 | 0.4 |
| RPA70-C-BE4max | Rep. 1 | 27.8 | 29.5 | 20.4 | 15.4 | 3.5 | 1.8 |
| | Rep. 2 | 28.1 | 29.4 | 20.9 | 15.7 | 3.8 | 1.9 |
| | Rep. 3 | 30.1 | 31.7 | 21.4 | 17 | 4.2 | 1.5 |

TABLE 5-continued

| Base editor | Repeat | C3 | C6 | C8 | C9 | C10 | C11 |
|---|---|---|---|---|---|---|---|
| | Results of editing efficiency of target Tim3-sg1 (in %) | | | | | | |
| RPA32-D-BE4max | Rep. 1 | 17.5 | 15.8 | 9.7 | 8.6 | 5.6 | 3.2 |
| | Rep. 2 | 17.9 | 16 | 9.9 | 8.8 | 5.8 | 3.3 |
| | Rep. 3 | 16.1 | 13.4 | 8.7 | 7.3 | 4.7 | 2.9 |
| BRCA2-OB2-BE4max | Rep. 1 | 9.2 | 9.3 | 7.9 | 7.3 | 6.2 | 5.6 |
| | Rep. 2 | 9.2 | 9.3 | 7.9 | 7.3 | 6.2 | 5.6 |
| | Rep. 3 | 8.8 | 9 | 7.4 | 7 | 5.6 | 4.7 |
| BRCA2-OB3-BE4max | Rep. 1 | 10.7 | 10.4 | 7.4 | 5.9 | 3.7 | 2.8 |
| | Rep. 2 | 13.1 | 10.1 | 8.2 | 7.7 | 4 | 2.6 |
| | Rep. 3 | 10.4 | 10 | 7.5 | 6.9 | 4.8 | 3.3 |
| KH-BE4max | Rep. 1 | 6.6 | 5.9 | 3.9 | 3.1 | 2.1 | 1.5 |
| | Rep. 2 | 6.5 | 5.9 | 4.1 | 3.1 | 2 | 1.5 |
| | Rep. 3 | 6.7 | 6.7 | 4.6 | 3.3 | 2.3 | 1.5 |
| RRM-BE4max | Rep. 1 | 8.1 | 6.9 | 4.8 | 3.8 | 2.5 | 1.6 |
| | Rep. 2 | 8 | 6.6 | 4.8 | 3.7 | 2.4 | 1.5 |
| | Rep. 3 | 7.7 | 7.1 | 5.2 | 4.5 | 3 | 2 |
| Rad51DBD-BE4max | Rep. 1 | 39.4 | 40.6 | 33.1 | 31.2 | 24.4 | 16.8 |
| | Rep. 2 | 39.2 | 40.6 | 32.7 | 30.7 | 23.6 | 16.6 |
| | Rep. 3 | 34.3 | 34.7 | 27.8 | 25.9 | 19.7 | 13.2 |
| hyBE4max | Rep. 1 | 49.5 | 49.2 | 49 | 50.1 | 49.1 | 47 |
| | Rep. 2 | 48.8 | 48.6 | 48.1 | 49.7 | 48.6 | 46.8 |
| | Rep. 3 | 43.3 | 42.6 | 43.4 | 44.5 | 44.1 | 41.8 |
| BE4max-C-Rad51 | Rep. 1 | 18.8 | 20.7 | 15.6 | 12.6 | 3.3 | 1.8 |
| | Rep. 2 | 18.9 | 20.4 | 15.6 | 12.7 | 3.5 | 1.9 |
| | Rep. 3 | 21.1 | 22.5 | 16.4 | 12.9 | 3.1 | 1.7 |
| Blank control | Rep. 1 | 0.1 | 0 | 0 | 0 | 0 | |
| | Rep. 2 | 0 | 0 | 0 | 0 | 0 | 0 |
| | Rep. 3 | 0 | 0 | 0 | 0 | 0 | 0 |

The results in Table 4 and Table 5 shown that, compared with Rad51 DBD fused between NLS and rA1 in BE4max (i.e., Rad51DBD-N-BE4max), Rad51 DBD fused between rA1 and spCas9n in BE4Max (i.e., hyBE4max) most obviously improves the C-to-T editing efficiency on targets.

3. Working Characteristics of hyBE4max

In order to further describe the working characteristics of hyBE4max fairly, 6 additional targets VEGFA site2, Lag3-sg2, HEK3, HEK4, EMX1-sg2p, and Nme1-sg1 (the sequences shown in Table 2) were designed and connected to BbsI site of plasmid U6-sgRNA-EF1α-GFP to obtain recombinant plasmids pV, pL, pH3, pH4, pEP and pN. Theses plasmids were sequenced by sanger to ensure that they are completely correct.

The recombinant plasmid containing hyBE4max in step 2 along with recombinant plasmids pE, pT, pV, pL, pH3, pH4, pEP or pN were respectively transfected into cells according to the method of 1.2 in step 1; the results of editing efficiency were obtained according to the methods of 1.3 and 1.4 in step 1; and statistical mapping was performed using Graph-Pad Prism 8.0.

Figure 2:
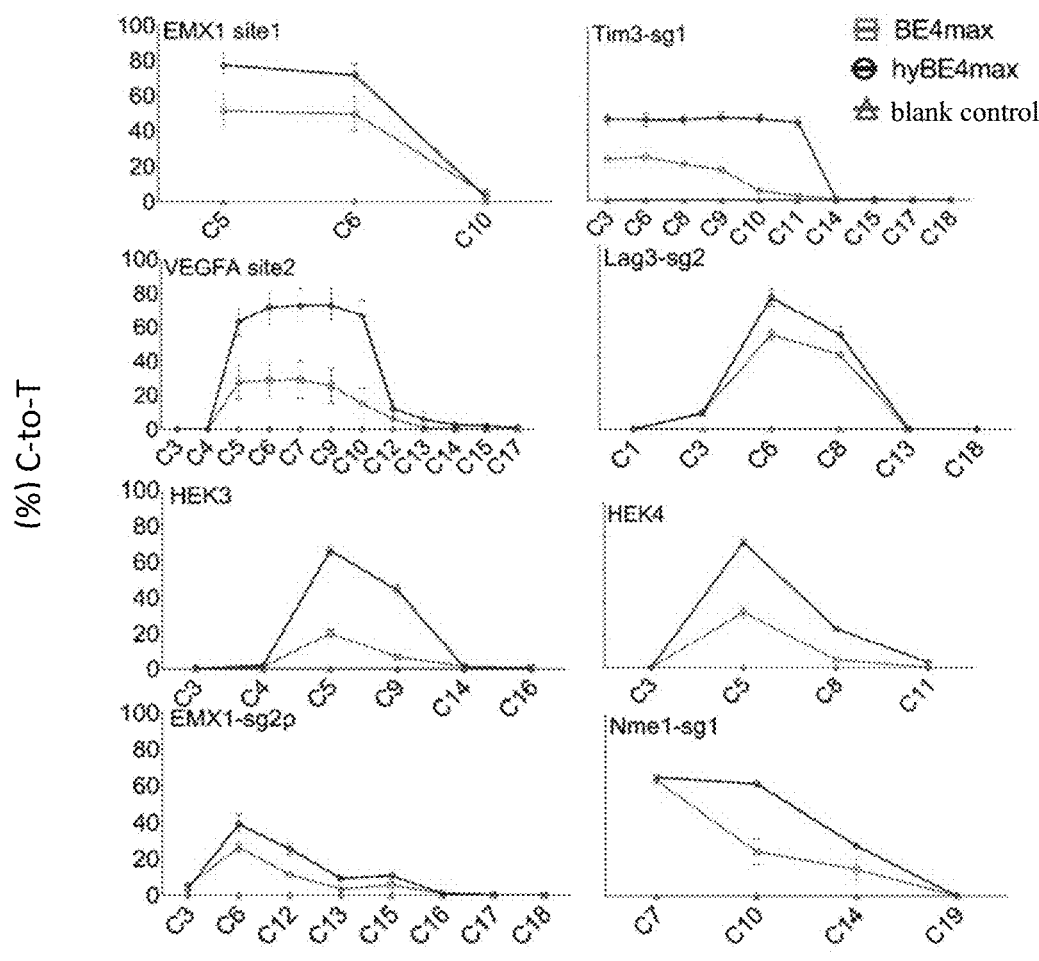
FIG. 2 shows the comparison of C-to-T base editing efficiency (i.e., ordinate, in %) achieved by hyBE4max and BE4max at 8 targets on 293T.
Figure 3:
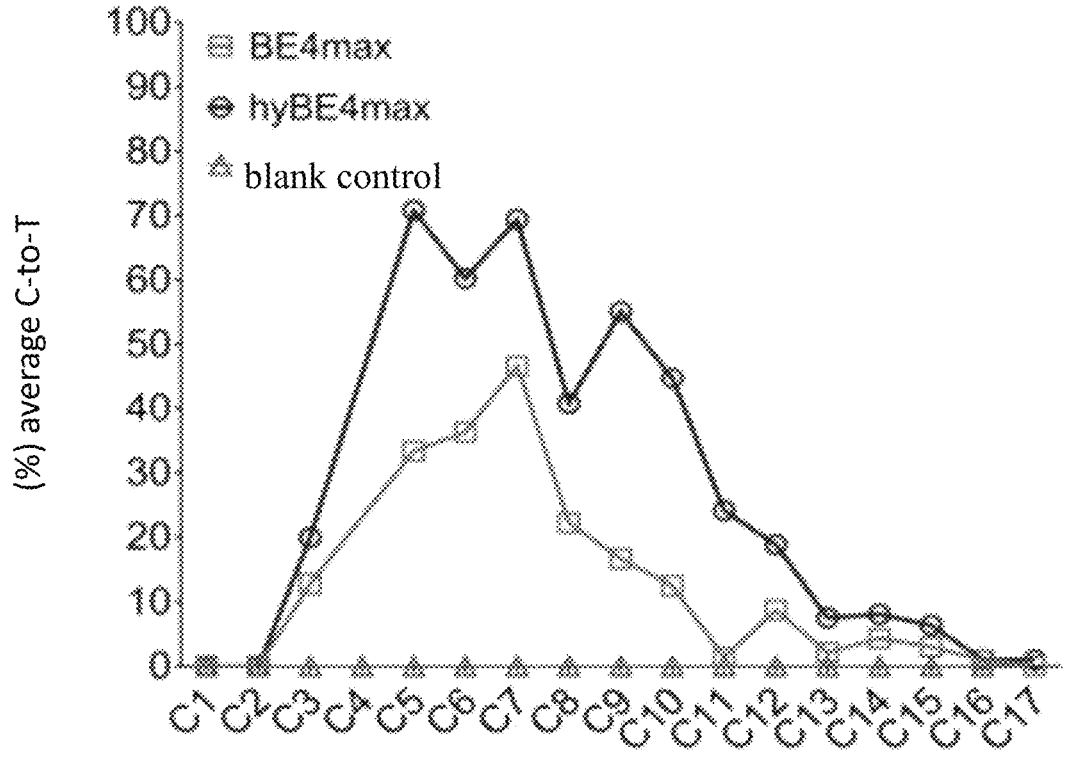
FIG. 3 shows the comparison of average C-to-T base editing efficiency (i.e., ordinate, in %) generated by hyBE4max and BE4max at 8 targets on 293T.
Figure 4:
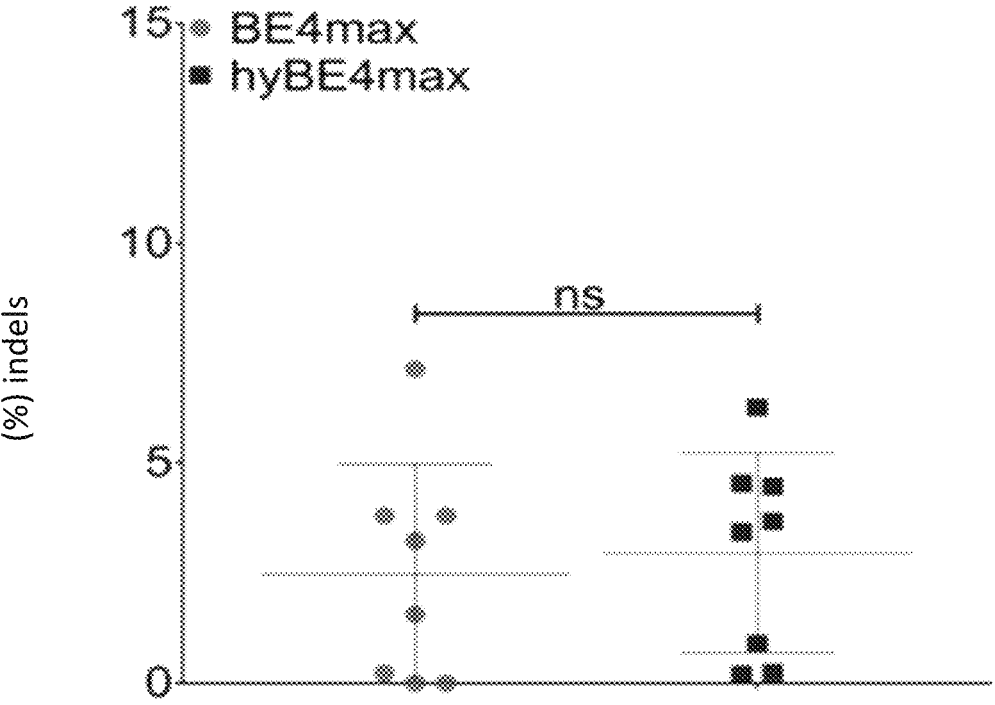
FIG. 4 shows the comparison of base editing efficiency (i.e., ordinate, in %) of indels generated by hyBE4max and BE4max at 8 targets on 293T.

The results were shown in FIGS. 2 and 3, in the editing windows C3-C8, the C-to-T editing efficiency of hyBE4max was 19-71%, and that of the corresponding BE4max was 13-47%; in the editing windows C9-C12, the C-to-T editing efficiency of hyBE4max was 19-55%, and that of the corresponding BE4max was 1.4-17%. Compared with BE4max, in the editing windows C3-C8, the average C-to-T editing efficiency of hyBE4max was 1.6-2.2 times that of BE4max; in the editing windows C9-C12, the average C-to-T editing efficiency of hyBE4max was 3.3-17 times that of BE4max. The production of indels maintained by hyBE4max was relatively low (FIG. 4).

4. Effects of Fusion Proteins Containing Different Cytosine Deaminase (1) Working Characteristics of Fusion Protein hyA3A-BE4max 4.1.1. Rad51-DBD was synthesized according to the coding sequences in Table 1, and then seamlessly cloned and assembled between hA3A and spCas9n in the plasmid pCMV-A3A-BE4max expressing protein A3A-BE4max (FIG. 5); and the recombinant plasmid pA expressing fusion protein hyA3A-BE4max (FIG. 5) was constructed.

4.1.2. 8 human endogenous targets were synthesized sequentially: the target sequences of EMX1 site1, Tim3-sg1, VEGFA site2, EMX1-sg2p, and Nme1-sg1 were shown in Table 2; the target sequences of FANCF site1, EGFR-sg5, and EGFR-sg21 were shown in Table 6; and recombinant plasmids pB1, pB2, . . . , pB8 expressing the corresponding targets of sgRNA were obtained by connecting them to Bbs I site of sgRNA-expression plasmid pU6-sgRNA-EF1α-GFP, respectively.

4.1.3. The plasmids constructed in 4.1.1 and 4.1.2 were sequenced by sanger to ensure that they are completely correct.

TABLE 6

| Targets and sequences used | | |
|---|---|---|
| Name of targets | Sequence (5'-3') | SEQ ID NO: |
| FANCFsite1 | GGAATCCCTTCTGCAGCACCTGG | 25 |
| EGFR-sg5 | GTGCTGGGCTCCGGTGCGTTCGG | 26 |
| EGFR-sg21 | CAAAGCAGAAACTCACATCGAGG | 27 |

4.1.4. Cell Transfection $5 \times 10^5$ HEK293T cells were plated into a 24-well plate. When the cells grew to 70%-80%, the plasmid combination were transfected according to pA (or plasmid pCMV-A3A-BE4max):pB1 (or pB2, pB3, . . . , pB8)=750 ng:250 ng. 3 replicate wells were set for transfection of each plasmid combination, with $2 \times 10^5$ cells per well. Simultaneously, a blank control without transfection of any plasmid was set.

4.1.5. Genome Extraction and Preparation of Amplicon Library

The procedure of step 1.3 was followed, wherein the identification primers for the targets of FANCF site1, EGFR-sg5 and EGFR-sg21 were shown in Table 7, and the other identification primers for expression were shown in Table 3.

TABLE 7

| Identification primers for targets used | |
|---|---|
| Name of targets | Sequence (5'-3') |
| FANCFsite1 | F: ggagtgagtacggtgtgc CAGAGAGGCGTATCATTTCGCGGAT R: gagttggatgctggatgg CCAGGTGCTGACGTAGGTAGTGCTT |
| EGFR-sg5 | F: ggagtgagtacggtgtgc CTTGTGGAGCCTCTTACACCCAGTG R: gagttggatgctggatgg CTCCCCACCAGACCATGAGAGGC |
| EGFR-sg21 | F: ggagtgagtacggtgtgc GCAGCATGTGGCACCATCTCA R: gagttggatgctggatgg TGGACCCCCACACAGCAA |

4.1.6. Analysis and Statistics of Deep Sequencing Results

The procedure of step 1.4 was followed.

Figures 5, 6:
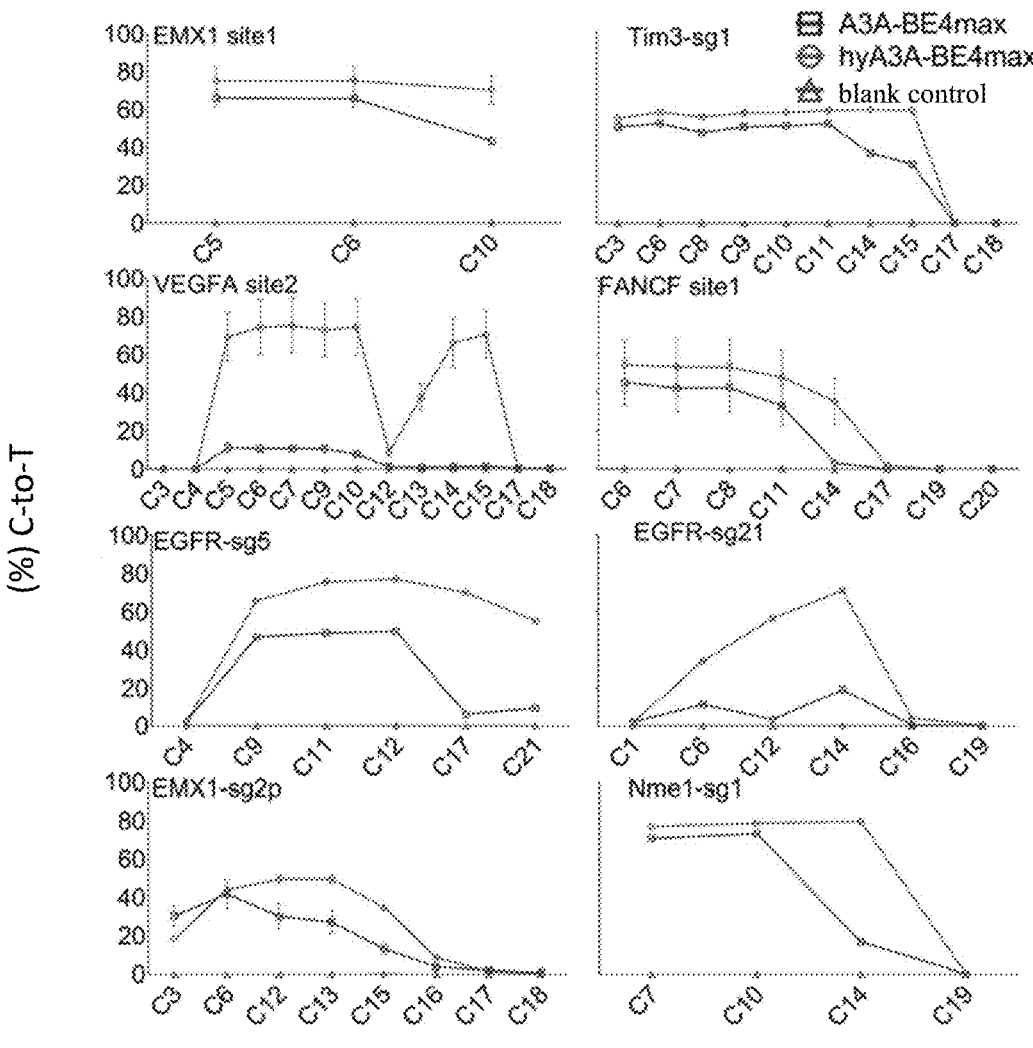
FIG. 5 shows a structural diagram of fusion proteins A3A-BE4max and hyA3A-BE4max, wherein hA3A is a human-derived cytidine deaminase APOBEC3A (its amino acid sequence is SEQ ID NO: 13 and coding sequence is SEQ ID NO: 14); and NLS, spCas9n and UGI were the same as those in FIG. 1.
FIG. 6 shows the comparison of C-to-T base editing efficiency (i.e., ordinate, in %) achieved by hyA3A-BE4max and A3A-BE4max at 8 endogenous targets on 293T.

The results show that, compared with the protein A3A-BE4max, the editing efficiency of single-base C-to-T at different positions (C3-C15) of individual targets was significantly improved by the fusion protein hyA3A-BE4max (FIG. 6). Compared with A3A-BE4max, the high activity windows of hyA3A-BE4max were expanded from the original C3-C11 to C3-C15; wherein the editing efficiency of single-base C-to-T by hyA3A-BE4max was 1.1-2.3 times that of A3A-BE4max at C3-C11 far away from PAM region, while the editing efficiency of single-base C-to-T by hyA3A-BE4max was 3.1-4.1 times that of A3A-BE4max at C12-C15 near PAM region; the editing efficiency of single-base C-to-T at C12-C15 near PAM region was more obviously improved by hyA3A-BE4max. And the indels maintained by hyA3A-BE4max were relatively low (FIG. 8).

(2) Working Characteristics of Fusion Protein hyeA3A-BE4Max 4.2.1. Construction of Working System Plasmid Rad51-DBD was synthesized according to the coding sequences in Table 1, and then seamlessly cloned and assembled between eA3A and spCas9n in the plasmid pCMV-eA3A-BE4max expressing the protein eA3A-BE4max (FIG. 9), and the recombinant plasmid pAe expressing the fusion protein hyeA3A-BE4max (FIG. 9) was constructed.

4.2.2. Construction of Target Plasmid

Meanwhile, 11 human endogenous targets were designed and synthesized: the target sequences of EMX1-sg2p, EMX1 site1, and Nme1-sg1 were shown in Table 2; the target sequence of EGFR-sg21 was shown in Table 6; and the other target sequences were shown in Table 8; which were respectively connected to BbsI site of sgRNA-expression plasmid U6-sgRNA-EF1α-GFP to express sgRNA of corresponding target, thus obtaining recombinant plasmids pC1, pC2, . . . , pC11.

4.2.3. The plasmids constructed in 4.2.1 and 4.2.2 were sequenced by sanger to ensure that they are completely correct.

TABLE 8

| | Targets and sequences used | |
|---|---|---|
| Name of targets | Sequence (5'-3') | SEQ ID NO: |
| CTLA-sg1 | CTCCCTCAAGCAGGCCCCGCTGG | 28 |
| EGFR-sg5 | GTGCTGGGCTCCGGTGCGTTCGG | 29 |
| CDK10-sg1 | TTCTCGGAGGCTCAGGTGCGTGG | 30 |
| EMX1-sg1 | GCTCCCATCACATCAACCGGTGG | 31 |
| HPRT1-sg6 | GCCCTCTGTGTGCTCAAGGGGGG | 32 |
| EGFR-sg26 | CATGCCCTTCGGCTGCCTCCTGG | 33 |
| CCR5-sg1 | TAATAATTGATGTCATAGATTGG | 34 |

4.2.4. Cell Transfection-Verification of hyeA3A-BE4Max Working System $5 \times 10^5$ HEK293T cells were plated into a 24-well plate. When the cells grew to 70%-80%, the plasmid combination were transfected according to pA (or plasmid pCMV-eA3A-BE4max):pC1 (or pC2, pC3, . . . , pC11)=750 ng:250 ng. 3 replicate wells were set for transfection of each plasmid combination, with $2 \times 10^5$ cells in each well. Simultaneously, a blank control without transfection of any plasmid was set.

4.2.5. Genome Extraction and Preparation of Amplicon Library

The procedure of step 1.3 was followed, wherein the identification primers for EMX1-sg2p, EMX1 site1 and Nme1-sg1 were shown in Table 3, the identification primers for EGFR-sg21 were shown in Table 7, and the other target sequences were shown in Table 9.

TABLE 9

| | Identification primers for targets used |
|---|---|
| Identification of primers | Sequence (5'-3') |
| CTLA-sg1 | F: GGAGTGAGTACGGTGTG CACTTTAACCCCAAGTCTAG CAAGC <br> R: GAGTTGGATGCTGGATG GATAATTAATCCAATGACTG TGAAGAGC |
| EGFR-sg5 | F: GGAGTGAGTACGGTGTG CCTTGTGGAGCCTCTTACAC CCAGTG <br> R: GAGTTGGATGCTGGATG GCTCCCCACCAGACCATGAG AGGC |
| CDK10-sg1 | F: GGAGTGAGTACGGTGTG CGGTGATGGGTTACTGTGAG CAGGAC <br> R: GAGTTGGATGCTGGATG GGTCCCCAAGTGCCCTGTTT CGTTAT |
| EMX1-sg1 | F: GGAGTGAGTACGGTGTG CGTGGTTCCAGAACCGGAGG ACAAAG <br> R: GAGTTGGATGCTGGATG GGTTTGTGGTTGCCCACCCT AGTCAT |
| HPRT1-sg6 | F: GGAGTGAGTACGGTGTG CTTCCTGATTTTATTTCTGT AGGACTG <br> R: GAGTTGGATGCTGGATG GTCTACAGTCATAGGAATGG ATCTATCA |
| EGFR-sg26 | F: GGAGTGAGTACGGTGTG CACCTCCACCGTGCAGCTC <br> R: GAGTTGGATGCTGGATG GAGCGCAGACCGCATGTGAG |
| CCR5-sg1 | F: GGAGTGAGTACGGTGTG CTGCACAGGGTGGAACAAGA TGGATT <br> R: GAGTTGGATGCTGGATG GATGACCAGCATGTTGCCCA CAAAAC |

4.2.6 Analysis and Statistics of Deep Sequencing Results

The procedure of step 1.4 was followed.

Figures 10, 11, 12:
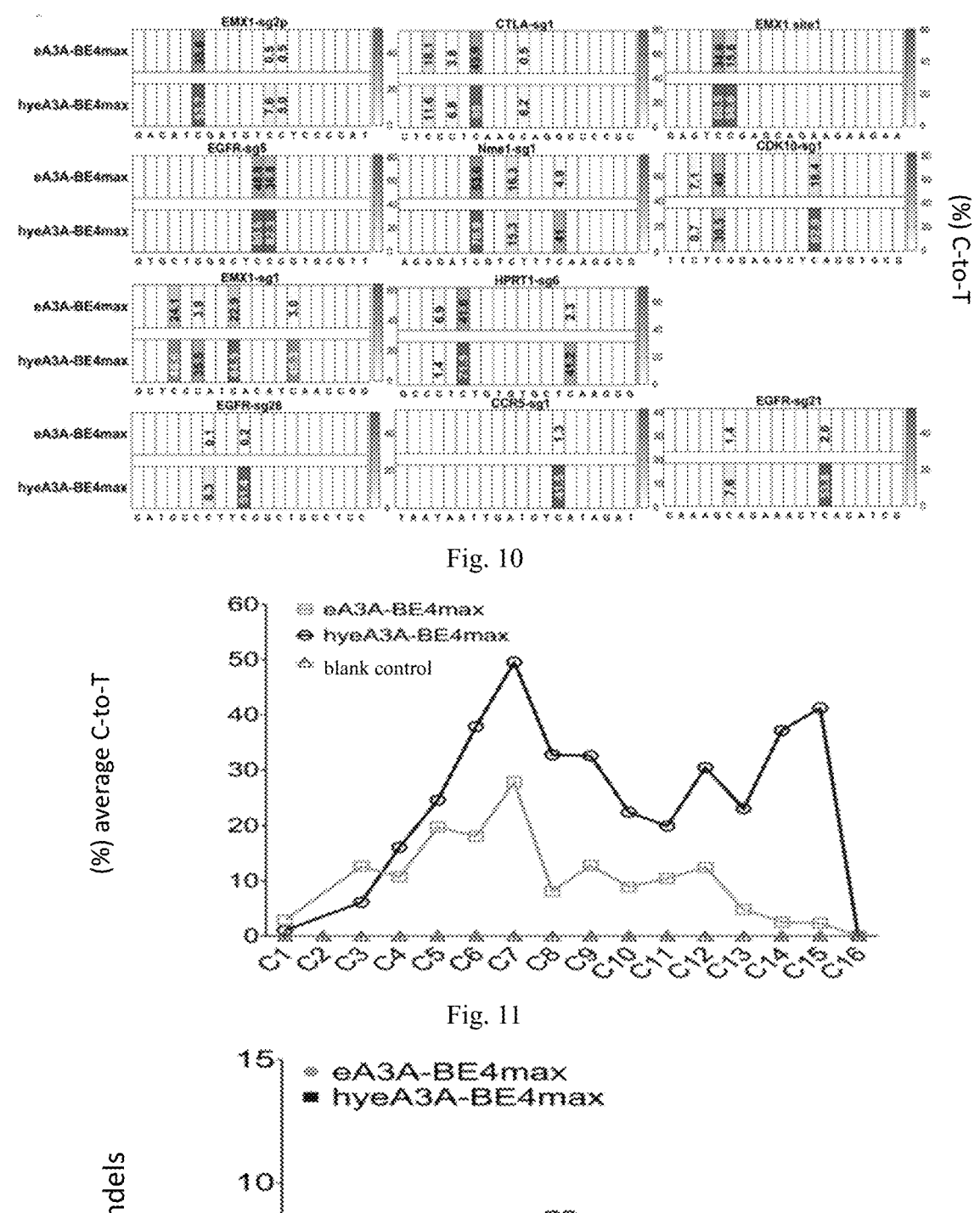
FIG. 10 shows the comparison of C-to-T base editing efficiency (i.e., ordinate, in %) achieved by hyeA3A-BE4max and eA3A-BE4max at 11 endogenous targets on 293T.
FIG. 11 shows the comparison of average C-to-T base editing efficiency (i.e., ordinate, in %) achieved by hyeA3A-BE4max and eA3A-BE4max at 11 endogenous targets on 293T.
FIG. 12 shows the comparison of base editing efficiency (i.e., ordinate, in %) of indels generated by hyeA3A-BE4max and eA3A-BE4max at 11 endogenous targets on 293T.

The results show that, compared with the protein eA3A-BE4max, the editing efficiency of single-base C-to-T at different positions (C3-C15) of individual targets was significantly improved by the fusion protein hyeA3A-BE4max, and the high activity windows were expanded from the original C3-C11 to C3-C15, which can specifically target the single base C in TC motif to achieve the C-to-T conversion (FIG. 10); wherein, in C3-C11 far away from PAM region, the editing efficiency of single-base C-to-T by hyeA3A-BE4max was 1.6-2.8 times that of eA3A-BE4max, and at C12-C15 near PAM region, the editing efficiency of single-base C-to-T by hyeA3A-BE4max was 4.5-31.9 times that of eA3A-BE4max, i.e., at C12-C15 near PAM region, the editing efficiency of single-base C-to-T was more obviously improved by hyeA3A-BE4max (FIG. 11). While the indels maintained by hyeA3A-BE4max were relatively low (FIG. 12).

5. Gene Therapy Using Fusion Protein hyeA3A-BE4max 5.1. Test of Editing Efficiency of hyeA3A-BE4max Targeting HBG-117G Sites on HEK293T Cells Transfected HEK293T cells with the plasmid combination according to the cell transfection method of 4.2.4, pA (or plasmid pCMV-A3A-BE4max, or pAe, or pCMV-eA3A-BE4max):pC12=750 ng:250 ng; and deep sequencing and statistical analysis were carried out according to the method of 4.2.6.

The construction method of the recombinant plasmid pC12 is as follows: the sgRNA target sequence of HBG-117G (GGCTATTGGTCAAGGCAAGGCTGG, SEQ ID NO: 35) was connected to the BbsI site of the sgRNA-expression plasmid U6-sgRNA-EF1α-GFP to express the sgRNA of corresponding target to obtain the recombinant plasmid pC12.

The identification primers used for the above deep sequencing target HBG-117G are as follows:

```
HBG-117G F:
AGTGAGTACGGTGTGCTGGAATGACTGAATCGGAACAAGGC;

HBG-117G R:
GTTGGATGCTGGATGGCTGGCCTCACTGGATACTCTAAGACT.
```

Results: as shown in FIG. 14, A3A-BE4max not only targeted the −117G>A (C11) mutation in the HBG1/2 promoter region, but also produced the −109G>A (C3), −122G>A (C16) "bystander" mutation; for eA3A-BE4max and hyeA3A-BE4max, eA3A-BE4max accurately edited the G-to-A conversion on −117 (i.e., the C-to-T conversion of complementary chain) without causing "bystander" mutation, but the efficiency was very low; and compared with eA3A-BE4max, hyeA3A-BE4max improved the G-to-A conversion efficiency by 6.6 times, and detectable "bystander" mutation was not produced at both −109 and −122. The results suggest that hyeA3A-BE4max exhibited the characteristics of targeting HBG1/2 promoter region −117G accurately and efficiently (the mechanism was summarized in FIG. 13).

5.2. Construction of Lentiviral Vector and Virus Packaging 5.2.1 Construction of Lentiviral Vector pLenti-BE3-P2A-Puro (Addgene, #110838) was used as skeletal vector, the coding sequence of hyA3A-BE4max was cloned seamlessly to replace BE3 on the skeletal vector to obtain lentiviral vector Lenti-hyA3A-BE4max-P2A-GFP.

pLenti-BE3-P2A-Puro (Addgene, #110838) was used as skeletal vector, the coding sequence of hyeA3A-BE4max was cloned seamlessly to replace BE3 on the skeletal vector to obtain a lentiviral vector Lenti-hyeA3A-BE4max-P2A-GFP.

The target sequence of HBG-117G in 5.2 was connected to the upstream of the above two lentiviral vectors hyA3A-BE4max or hyeA3A-BE4max (top figure of FIG. 15) to obtain a recombinant plasmid Lenti-117G-hyA3A-BE4max-P2A-GFP and a recombinant plasmid Lenti-117G hyeA3A-BE4max-P2A-GFP (bottom figure of FIG. 15).

5.2.2. Lentiviral Packaging 5.2.2.1. Transfection

On the 1st day, HEK293T cells in good growth condition were digested and placed in 10 cm dishes, with about 30 dishes for each virus. On the 2nd day, when the confluence reached 80%-90%, the plasmid was transfected with following amount: Lenti-117G-hyA3A-BE4max-P2A-GFP (or Lenti-117G-hyeA3A-BE4max-P2A-GFP):PSPAX2: PMD2.G=10 µg:10 µg:10 µg.

5.2.2.2. Collection and Purification of Virus

The virus supernatant was collected from HEK293T cell supernatant at 48 h (i.e., 0 h was recorded from transfection) and 72 h after transfection. The supernatant was centrifuged at 4° C. under 4000 g for 10 min, the cell debris was removed, then the supernatant was filtered through a 0.45 µm filter into a 40 mL ultrafiltration centrifuge tube, the lentiviral crude extract was added into a filter cup and centrifuged at 4° C. under 25000 g for 2.5 hours. After the centrifugation, the centrifugal device was taken out, and filter cup was separated from the filtrate collection cup. The liquid in the sample collection cup is concentrated virus liquid (containing lentivirus Lenti-117G-hyA3A-BE4max-P2A-GFP or lentivirus Lenti-117G-hyeA3A-BE4max-P2A-GFP). The concentrated virus liquid was removed, subpackaged and stored in a virus tube, and preserved at −80° C. for long-term storage.

5.3. Gene Therapy 5.3.1. HUDEP-2 ($\Delta^G\gamma$) Cells Infected with Virus $5\times10^4$ HUDEP-2 ($\Delta^G\gamma$) cells were plated in culture medium with a total volume of 100 µl in 3 wells in a 96-well plate, and then infected with lentivirus Lenti-117G-hyA3A-BE4max-P2A-GFP and Lenti-117G-hyeA3A-BE4max-P2A-GFP in equal titer, respectively. The infection system is as follows:

| Reagents | Lenti-117G-hyA3A-BE4max-P2A-GFP | Lenti-117G-hyeA3A-BE4max-P2A-GFP | Blank control |
|---|---|---|---|
| virus | 10 MOI | 10 MOI | 0 |
| Polybrene (100×) | 1 µl | 1 µl | 1 µl |
| Culture medium | Added up to 100 µl | | |

5.3.2. Detection of Editing Efficiency

The HUDEP-2 ($\Delta G\gamma$) cells infected with lentivirus Lenti-117G-hyA3A-BE4max-P2A-GFP or Lenti-117G-hyeA3A-BE4max-P2A-GFP were sorted by flow cytometry to obtain GFP-positive cells, the GFP-positive cells were cultured, and then collected after the number of cells was more than $5\times10^4$, the genomic DNA was extracted, and the deep sequencing and analysis were carried out according to the method of 5.1.

Results: compared with hyA3A-BE4max, hyeA3A-BE4max efficiently targeted the precise −117G>A mutation in HUDEP-2 ($\Delta G\gamma$) cells and shown higher activity (FIG. 16).

5.3.3 Differentiation and Detection of γ Globin Expression

The HUDEP-2 ($\Delta G\gamma$) cells infected with lentivirus Lenti-117G-hyA3A-BE4max-P2A-GFP or Lenti −117G-hyeA3A-BE4max-P2A-GFP were sorted by flow cytometry to obtain GFP-positive cells, the GFP-positive cells were cultured until the number of cells was more than $5\times10^4$, and HUDEP-2 ($\Delta^G\gamma$) cells were collected after about 5-7 days for differentiation and expression. The differentiation process is as follows:

$1\times10^5$ HUDEP-2 ($\Delta^G\gamma$) cells after being counted were differentiated in erythroid cell differentiation medium (IMDM), supplemented with 2% human blood AB-type plasma (serum) (Gemini, 100-512), 1% L-glutamine, 2 IU/mL of heparin, and erythropoietin (EPO, 3 IU/mL, PeproTech), 330 µg/mL Holo-human transferrin (Sigma-Aldrich), human stem cell factor (SCF, 50 ng/mL, Pepro- Tech), 2% Pen/Strep (Gibco), and 10 μg/mL recombinant human insulin; the cells were then differentiated for 8 days.

Detection of γ globin expression: the cells were collected after 8 days of differentiation and total mRNA was extracted by phenol-chloroform extraction method. HiScript II Q RT SuperMix (Vazyme) was used to reversely transcribe the isolated mRNA; qPCR was performed on QuantiStudio 3 real-time PCR system (ABI), and mRNA levels of HBG and HBB were quantified by SYBRGreen qPCR. The primers (5'-3') are as follows:

```
HBG-QPCR-F:
GGTTATCAATAAGCTCCTAGTCC;

HBG-QPCR-R:
ACAACCAGGAGCCTTCCCA;

HBB-QPCR-F:
TGAGGAGAAGTCTGCCGTTAC;

HBB-QPCR-F:
ACCACCAGCAGCCTGCCCA.
```

Results: compared with WT cells of HUDEP-2 ($\Delta^G\gamma$), hyA3A-BE4max and hyeA3A-BE4max could significantly increase the mRNA level of γ-globin in HUDEP-2 ($\Delta G\gamma$) cells; and hyeA3A-BE4max increased the mRNA level of γ-globin in HUDEP-2 ($\Delta G\gamma$) cells by 3 times as much as that of hyA3A-BE4max (FIG. 17).

6. Using Fusion Protein hyA3A-BE4max to Construct Animal Model of DMD Disease

The mice used below are C57/BL6 mice.

6.1. Construction of Transcription Template for Working System mRNA and Target sgRNA A mouse-related gene sequence was download at NCBI, as shown in FIG. 18, a sgRNA (DMD-sg3 target sequence: ACATCTCATCAAGGACTTGTTGG, SEQ ID NO: 36) was designed at the target site (dystrophin gene, i.e., the site in the rectangle frame of exon 12 of DMD gene), and Oligo primers were ordered; the sgRNA formed by annealing was cloned into T7 vector selekton, and the DMD-sg3 template containing T7 promoter was amplified via in vitro transcription (IVT) using primer pairs IVT-PCR-F and IVT-PCR-R (Table 10), and primer pairs IVT-T7-hyA3A-BE4max-F and IVT-T7-hyA3A-BE4max-R (Table 10) were used to introduce T7 promoter into the mRNA template of hyA3A-BE4max or A3A-BE4max by PCR.

TABLE 10

PCR primers used in IVT

| Primer name | Primer sequence (5'-3') |
|---|---|
| IVT-PCF-F | GCGGCTTTGTTGAATAAATCGCATTCG |
| IVT-PCF-R | AAAAGCACCGACTCGGTGCC |
| IVT-T7-hyA3A-BE4max-F | TTAATACGACTCACTATAGGGAGAATG AAGAGGACCGCCGATGGCTC |
| IVT-T7-hyA3A-BE4max-R | CTAGTCACCTCCCAGCTGAGACAGGTC |

6.2. In Vitro Transcription of sgRNA (DMD-sg3)

A common DNA product purification kit was used to purify the PCR product in 6.1, the purified PCR product was then used as a linearized DNA template and T7 in vitro transcription kit (MEGAshortscript™ Kit) was used to carry out in vitro transcription. The transcribed sgRNA was purified by using lithium chloride precipitation method.

6.3. Transcription of Working System mRNA (A3A-BE4max and HyA3A-BE4max)

T7 templates of A3A-BE4max and hyA3A-BE4max were transcribed in vitro using the in vitro RNA transcription kit (mMESSAGE mMACHINE®T7 Ultra Kit) to obtain the working system mRNA, which was then purified.

6.4. Preparation of Microinjection Mixture

An injection mixture was prepared with nuclease-free water to obtain a mixture with a total volume of 20 μL. The injection mixture contains working system mRNA (mRNA containing A3A-BE4max or hyA3A-BE4max) with a final concentration of 100 ng/μL and sgRNA (DMD-sg3) with a final concentration of 200 ng/μL.

6.5. Collection of One-Cell Stage Embryos (1) The $1^{st}$ day: donor female mice aged 6-8 weeks were intraperitoneally injected with 100 μL (5 IU) of PMSG working solution between 1 p.m. and 2 p.m.

(2) The $3^{rd}$ day: 100 μL (5 IU) of hCG working solution was intraperitoneally injected into the female mice between 2 p.m. and 4 p.m. that had been injected with PMSG. After the injection, the hormone-treated female mice were co-caged one-to-one with male mice aged 10-14 weeks. Meanwhile, the estrous hormone-free female mice were mated with the tubal ligated male mice at around 4 p.m. for the preparation of pseudopregnant female mice.

(3) The $4^{th}$ day: before 9 a.m., the recipient female mice that were co-caged with the ligated male mice were examined for the presence of pregnancy plugs, and the female mice having pregnancy plugs were collected in new cages for embryo transfer experiment in the afternoon.

(4) The superovulatory female donor mice were sacrificed by carbon dioxide asphyxiation method, and their oviducts were taken out and placed in dishes in which preheated M2 medium was added.

(5) The oviducts were placed in another new dish, and preheated M2 medium and hyaluronic acid were added into the dish with the volume ratio of M2 medium to hyaluronic acid being 9:1. The ampullae of the oviducts were pulled with tweezers under a stereomicroscope to release the embryos from the oviducts into the dish. Embryos were incubated in M2 medium containing hyaluronic acid until cumulus cells dropped. After the cumulus cells were removed, the embryos were transferred to a new dish, and M2 medium without hyaluronic acid was added into the dish, and the embryos were repeatedly rinsed with M2 medium to wash out both hyaluronic acid and cumulus cells.

(6) The washed embryos were transferred to a new dish, a few drops of KSOM medium was firstly added dispersedly into the dish, and then mineral oil was slowly added into the dish to separate and cover the KSOM medium with the mineral oil. In general, 6 droplets of KSOM medium can be added into a 35 mm dish with each droplet being 50 μL. 50 embryos as a group were placed firstly onto the middle KSOM medium droplets and rinsed, and then transferred to a new medium droplet. The embryos before microinjection were taken out and incubated in M2 medium in a cell incubator.

6.6. Microinjection and Embryo Transfer (1) Fixing needle, injection needle and silicified glass slide were prepared, and a drop of M2 medium covered with mineral oil was dropped into the middle of the slide.

(2) The injection needle was allowed to automatically suck and filled with the microinjection mixture prepared in step 2.4 by capillary action, and the injection needle was loaded onto the fixed handle of the microinjection apparatus.

(3) 50 embryos were transferred into M2 medium on the glass slide, and the fixing needle was moved close to the embryos, so that the embryos could be fixed onto the fixing needle under negative pressure. After the embryos were fixed, the cytoplasm was found under a high-power microscope, and the tip of the injection needle was pushed through the zona pellucida and cell membrane, and the mixture was injected into the cytoplasm of the embryo.

(4) The injected embryonic cells were transferred to a new droplet of M2 medium. The steps (3) and (4) were repeated until all embryos were injected. After injection of a group of experimental groups, the embryos were transferred to new KSOM medium and incubated in a cell incubator for 1-2 hours or overnight. After all the embryos were injected, the embryos killed by mechanical damage were excluded, and the healthy embryos were transferred to new KSOM medium.

(5) The pseudopregnant rats were anesthetized by intraperitoneal injection of 600 μL avertin. A shaver was used to remove the hair from the back of the mice. The skin after being shaved was wiped with 70% ethanol.

(6) A small opening was formed by cutting at the position of the ovary, blunt forceps were used to pull the fat pad of the ovary to pull the ovary out, and at the same time the ovary was fixed to the outside with hemostatic forceps, and blunt forceps were used to find the funnel-shaped orifice of the oviduct at the lower side of the ovarian bursa.

(7) Transfer needle was used to sequentially suck M2 medium with two small bubbles, and about 15 embryos, and the bubbles were for observing the position of embryos in the transfer needle.

(8) Ovarian bursa was gently opened, the funnel-shaped orifice of the oviduct was positioned using a shaft, the transfer needle was extended to the opening of the ovary, then the embryo in the transfer needle was punched out, and the transfer needle was gently withdrawn.

(9) The hemostatic forceps fixing the fat pad of the ovary was released, the ovary was put back into the original cavity, and the muscle opening and the skin opening were sewn respectively with sutures.

(10) The mice after surgery were placed on a heat-preserving table with a constant temperature of 37 degrees; the mice were transferred to a feeding cage for feeding after the mice regained consciousness, followed by waiting for embryo development until delivery. Typically, the successfully transplanted female mice gave birth after 3 weeks.

6.7. Identification of Mouse Genome

The mice (in step 6.6) born about 10-15 days was taken and their toes were cut for genome identification. The specific steps are as follows:

6.7.1 Genomic Extraction (1) Their toes were cut and put into 1.5 mL centrifuge tubes, into which 500 μL of toe digestion liquid was added. The digestion liquid was prepared according to the ratio of protease K:tissue lysate=1:500, and then the tubes were placed in a water bath at 55° C. overnight;

(2) The toes digested overnight were taken out and placed at room temperature for 10-15 minutes, mixed thoroughly upside down, and centrifuged at 13000 rpm for 15 minutes.

(3) 400 μL supernatant was sucked out from each tube, an equal volume of chloroform was added, fully mixed. After DNA precipitation, the mixture was centrifuged at 12000 rpm for 10 minutes.

(4) 200 μL of 75% alcohol pre-cooled in a refrigerator at −20° C. was added into each tube and mixed gently, then centrifuged at 12,000 rpm for 5 min, and the supernatant was discarded, followed by air-drying in a clean workbench.

(5) 50-100 μL of deionized ultra-pure water was added according to the content of DNA, and the DNA was dissolved at 55° C. for 2 hours to obtain PCR template.

6.7.2 Identification of Genome

Primer pair F/R of target DMA-sg3 (Table 11) was used to obtain a DNA fragment containing the target; firstly, the occurrence of double peaks was confirmed by first-generation sequencing, and then the editing efficiency was obtained by high-throughput deep sequencing. According to the high-throughput results, among the 10 F0s producing mutations in the hyA3A-BE4max treatment group, there were 6 homozygous terminating nonsense mutations from CAA to TAA (the mice numbered #BD03, #BD05, #BD07, #BD12, #BD15, and #BD16 in the lower figure of FIG. 19), while no terminating nonsense mutation was found in the F0 in the A3A-BE4max treatment group (upper figure of FIG. 19). The HYA3A-BE4max treatment group had a higher number of Reads (high-throughput sequencing fragments) containing the stop codon TAA as a percentage of total Reads in homozygous mutations compared to the A3A-BE4MAX treatment group (FIG. 20).

TABLE 11

| Name of targets | Sequence (5'-3') |
|---|---|
| DMD-sg3 | F: ggagtgagtacggtgtgcTCA<br>AACTCCCAATGATTTCCTCAAT<br>R: gagttggatgctggatggTGC<br>ACTTCAGCTTCTTCATCTTCTG |

6.8. Phenotype Identification of DMD Gene

Wild-type mice of 5 weeks old (blank control) and mice with DMD gene mutation identified in 2.7.2 were taken, and immunohistochemical detection was carried out according to the following methods:

The tibialis anterior muscles of mice was taken and rinsed with alcohol and PBS. They were placed into a small cube box covered with OTC gel and placed into an isopentane beaker, followed by freezing in liquid nitrogen for about 30 s, taking out and storing at −20° C., and then freezing and sectioning. The prepared sections were washed with PBST for 3 times/5 min, oil circles were drawn at the aligned positions of tissues. The sections were blocked by adding blocking solution, and after 1 h of blocking, the sections were incubated overnight with Laminin primary antibody or Dystrophin primary antibody (Abcam, ab11575 or Abcam, ab15277 diluted at 1:500), respectively. The sections were washed with PBST for 3 times/5 min, followed by incubation with 1:1000 anti-rabbit diluted secondary antibody for 2 h, and then washed with PBST for 3 times/5 min. DAPI diluted at 1:100 was added and incubated for 10 min, and then washed with PBST for 3 times/5 min. Followed by dropwise adding anti-quenching agent, adding a cover glass, sealing with nail polish, and finally observing the fluorescence of the sections with a fluorescence microscope.

The results show that, compared with the mice of WT (+/+) and A3A-BE4max-treated mice (such as #AD26), only six F0-generation mice (such as #BD03 in FIG. 21) in the hyA3A-BE4max-treated mice that caused C-to-T homozygous nonsense mutation at position 10 of DMA-sg3 target sequence shown no protein expression of DMD (FIG. 21), which also proved that the animal model of DMD disease was constructed successfully.

According to the fluorescence observation results, a summary of F0 generation mice produced by editing hyA3A-BE4max and A3A-BE4max was obtained (as shown in Table 12).

TABLE 12

| | Comparison of F0 mutation results after editing hyA3A-BE4max and A3A-BE4max | |
|---|---|---|
| | Mutation frequency | |
| treatment | Proportion of mutated mice | Proportion of homozygous nonsense mutation |
| A3A-BE4max | 10/11 (91%) | 0/11 (0) |
| hyA3A-BE4max | 10/10 (100%) | 6/10 (60%) |

6.9. Genetic Analysis of Germ Line of DMD Mutant Mice (F0→F1)

The homozygous female mice #BD12 (F0) with DMD phenotype were mated with male wild-type mice, 8 homozygous F1 mice were obtained, and the genotypes of the born F1 were identified; and sanger sequencing results show that the Reads frequency of nonsense mutation produced in each F1 exceeded 96%, i.e., this nonsense mutation could be stably inherited to F1 generation (FIG. 22).

6.10. Off-Target Detection

Off-target primers were designed by using a Cas-OFFinder function on a CRISPR RGEN Tools website (http://www.rgenome.net) (Table 13): firstly, the PAM type of the tested tool and the species type to be tested (for example, for a mouse, being Mus musculus (mm10)-Mouse) were selected, then, the designed sgRNA sequence with a PAM portion removed was filled in the box of Query Sequences, the mismatched bases were selected to be within 3, and the resulting DNA Bulge Size was within 1, and then the corresponding off-target primers were obtained after submission.

The off-target primers described above were used to implement PCR respectively on the genomic DNA of F0 mice that have been edited by hyA3A-BE4max (with WT as blank control), and then the products were subjected to high-throughput deep sequencing to obtain the results for the off-target efficiency (FIG. 23).

TABLE 13

| Off-target sites of DMD-sg3 and PCR primers | | |
|---|---|---|
| Name of off-target sites | Target sequence (5'-3') | Primer sequence (5'-3') |
| DMD-sg3-OT1 | acatttaatcaaggc cttgttgg | F: ggagtgagtacg gtgtgcaaaagccta caacacaatgagaaa c<br>R: gagttggatgct ggatggttgataagg ctctaccaatgtgaa c |
| DMD-sg3-OT2 | acctgtcatcaagca cttgttgg | F: ggagtgagtacg gtgtgcaaggaatga ccttgcagagactgc c<br>R: gagttggatgct ggatggtgctcagtc ccatggatgactgtg a |
| DMD-sg3-OT3 | tcctgtcatcaagga cttgttgg | F: ggagtgagtacg gtgtgcgggtgcagag actgaagaaaaggcc a<br>R: gagttggatgct ggatggtctatctct |

TABLE 13-continued

| Off-target sites of DMD-sg3 and PCR primers | | |
|---|---|---|
| Name of off-target sites | Target sequence (5'-3') | Primer sequence (5'-3') |
| | | gagtatgtcaggcac tgg |
| DMD-sg3-OT4 | tcctctcatcaagca cttgttgg | F: ggagtgagtacg gtgtgcggaatgacc atccagagacttccc c<br>R: gagttggatgct ggatgggttggggacc ctatgctcagtccaa t |
| DMD-sg3-OT5 | acatctcacccagga cctgtggg | F: ggagtgagtacg gtgtgcggcttcctt ttctgtcactgtggg a<br>R: gagttggatgct ggatgggggggactgc cactcctaactttca t |
| DMD-sg-OT6 | acttctcatcaagga cctctggg | F: ggagtgagtacg gtgtgctccctatcc gtcttagtctggagc c<br>R: gagttggatgct ggatggacaagaaac catgcatcagcttgt ga |
| DMD-sg3-OT7 | acttctcatcaagga cctctggg | F: ggagtgagtacg gtgtgcgcagaaaga aagtacagacactta ca<br>R: gagttggatgct ggatggaatgggtaa atagttaaaagccat ga |
| DMD-sg3-OT8 | acaactcaaaaagga cttgttgg | F: ggagtgagtacg gtgtgcggctaccat aggccattttctgca t<br>R: gagttggatgct ggatggtgagaatga atgttaggtcaggtg ga |
| DMD-sg3-OT9 | acatctcatctatga tttgtagg | F: ggagtgagtacg gtgtgcggcttgccc aagtttattaggga gt<br>R: gagttggatgct ggatggccagcccct tggcctcctttaaaa t |
| DMD-sg3-OT10 | acaactcctcatgga cttgtggg | F: ggagtgagtacg gtgtgcacatcccag agaatcctgagttta aga<br>R: gagttggatgct ggatggtgctaggag agatggttgtatcaa gga |
| DMD-sg3-OT11 | gcatctcatctagga cttggtgg | F: ggagtgagtacg gtgtgctgtgatagg tgatttctcatgcac ca<br>R: gagttggatgct ggatggatcacattc acttcccttcacccc g |

TABLE 13-continued

| Off-target sites of DMD-sg3 and PCR primers | | |
|---|---|---|
| Name of off-target sites | Target sequence (5'-3') | Primer sequence (5'-3') |
| DMD-sg3-OT12 | aaatctcatcaatta cttgtagg | F: ggagtgagtacg gtgtgccagccttat ccatttacttgtgaa ttt<br>R: gagttggatgct ggatggtcaagaaca ataaaacaaatgaca gc |
| DMD-sg3-OT13 | tcatgtcagcaagga cttgttgg | F: ggagtgagtacg gtgtgcatgaccatc cagagactgacccac t<br>R: gagttggatgct ggatggccacttctg tattagtctggcact ggc |
| DMD-sg3-OT14 | acatctgaccaaggg cttgtagg | F: ggagtgagtacg gtgtgccagttcctg tcggcagttcctcaa t |

TABLE 13-continued

| Off-target sites of DMD-sg3 and PCR primers | | |
|---|---|---|
| Name of off-target sites | Target sequence (5'-3') | Primer sequence (5'-3') |
| | | R: gagttggatgct ggatggtgtgccctg gaaaagatcacacag a |
| DMD-sg3-OT15 | acttctcagcaagca cttgtagg | F: ggagtgagtacg gtgtgccaacggtag cctaaggactgtcca c<br>R: gagttggatgct ggatggcaggcttcc tgactttcaaaaccg c |

The results in FIG. 23 show that, compared with the blank control, the fusion proteins hyA3A-BE4max and DMD-sg3 substantially did not produce C-to-T editing on the 15 sites similar to DMD-sg3 targets in Table 13, i.e., the fusion proteins hyA3A-BE4max and DMD-sg3 in the present application substantially did not produce off-target effect.

What is claimed is:

1. A fusion protein for improving gene editing efficiency, comprising functional domain of a single-stranded DNA binding protein, a nucleoside deaminase and a nuclease, wherein the nucleoside deaminase is located at the N terminal of the nuclease, and wherein the functional domain of the single-stranded DNA binding protein is located between the nucleoside deaminase and the nuclease.

2. The fusion protein according to claim 1, wherein the non-sequence-specific single-stranded DNA binding protein is selected from any one of RPA70, RPA32, BRCA2, hnRNPK, PUF60 and Rad51; and the sequence-specific single-stranded DNA binding protein is selected from any one of TEBP, Teb1 and POT1.

3. The fusion protein according to claim 1, wherein the functional domain of the single-stranded DNA binding protein comprises any one of the following four domains: OB fold, KH domain, RRMS and whirly domain of the single-stranded DNA binding protein.

4. The fusion protein according to claim 1, wherein the functional domain of the single-stranded DNA binding protein comprises DNA binding domain of Rad51 or DNA binding domain of RPA70.

5. The fusion protein according to claim 4, wherein amino acid sequence of the DNA binding domain of Rad51 comprises a sequence of SEQ ID NO: 1;

or, coding sequence of the DNA binding domain of Rad51 comprises a sequence of SEQ ID NO: 2.

6. The fusion protein according to claim 4, wherein amino acid sequence of the DNA binding domain of RPA70 comprises a sequence of SEQ ID NO: 11;

or, coding sequence of the DNA binding domain of RPA70 comprises a sequence of SEQ ID NO: 12.

7. The fusion protein according to claim 1, wherein the nucleoside deaminase comprises cytosine deaminase or adenosine deaminase.

8. The fusion protein according to claim 7, wherein the cytosine deaminase comprises rat-derived cytosine deaminase.

9. The fusion protein according to claim 8, wherein amino acid sequence of the rat-derived cytosine deaminase comprises a sequence of SEQ ID NO: 3;

or, coding sequence of the rat-derived cytosine deaminase comprises a sequence of SEQ ID NO: 4.

10. The fusion protein according to claim 7, wherein the cytosine deaminase comprises human-derived cytosine deaminase APOBEC3A.

11. The fusion protein according to claim 10, wherein the amino acid sequence of the human-derived cytosine deaminase APOBEC3A comprises a sequence of SEQ ID NO: 13;

or, coding sequence of the human-derived cytosine deaminase APOBEC3A comprises a sequence of SEQ ID NO: 14.

12. The fusion protein according to claim 7, wherein the cytosine deaminase comprises the mutant of the cytosine deaminase APOBEC3A, and the mutant mutates asparagine at position 57 of the cytosine deaminase APOBEC3A into glycine.

13. The fusion protein according to claim 12, wherein the cytosine deaminase APOBEC3A is derived from a human.

14. The fusion protein according to claim 13, wherein amino acid sequence of the cytosine deaminase APOBEC3A comprises the sequence of SEQ ID NO: 13;

or, coding sequence of the cytosine deaminase APOBEC3A comprises the sequence of SEQ ID NO: 14.

15. The fusion protein according to claim 12, wherein amino acid sequence of the mutant of the cytosine deaminase APOBEC3A comprises a sequence of SEQ ID NO: 15;

or, coding sequence of the cytosine deaminase APOBEC3A comprises a sequence of SEQ ID NO: 16.

16. The fusion protein according to claim 1, wherein the nuclease is selected from one or more of Cas9, Cas3, Cas8a, Cas8b, Cas10d, Cse1, Csy1, Csn2, Cas4, Cas10, Csm2, Cmr5, Fok1 and Cpf1.

17. The fusion protein according to claim 16, wherein the nuclease is Cas9.

18. The fusion protein according to claim 17, wherein the Cas9 is selected from Cas9 derived from *Streptococcus pneumoniae, Staphylococcus aureus, Streptococcus pyogenes* or *Streptococcus thermophilus.*

19. The fusion protein according to claim 17, wherein the Cas9 is selected from Cas9 mutants VQR-spCas9, VRER-spCas9 or spCas9n.

20. The fusion protein according to claim 19, wherein amino acid sequence of spCas9n comprises a sequence of SEQ ID NO: 5;

or, coding sequence of the spCas9n comprises a sequence of SEQ ID NO: 6.

21. The fusion protein according to claim 1, wherein the fusion protein further comprises an NLS.

22. The fusion protein according to claim 21, wherein the NLS is located at at least one terminal of the fusion protein.

23. The fusion protein according to claim 21, wherein amino acid sequence of the NLS comprises a sequence of SEQ ID NO: 7;

or, coding sequence of the NLS comprises a sequence of SEQ ID NO: 8.

24. The fusion protein according to claim 1, wherein the fusion protein further comprises more than two copies of UGI.

25. The fusion protein according to claim 24, wherein the UGI is located at at least one terminal of the fusion protein.

26. The fusion protein according to claim 24, wherein amino acid sequence of the UGI comprises a sequence of SEQ ID NO: 9;

or, coding sequence of the UGI comprises a sequence of SEQ ID NO: 10.

27. A recombinant cell or recombinant bacterium containing the fusion protein according to claim 1.

28. The biomaterial according to claim 27, wherein the cells are T cells, hematopoietic stem cells, bone marrow cells, red blood cells or red blood cell precursor cells.

29. An sgRNA for gene editing of a target gene in cells, wherein the target sequence of the sgRNA comprises at least one of SEQ ID NO: 17-36.

30. The sgRNA according to claim 29, wherein the cells are T cells, hematopoietic stem cells, bone marrow cells, red blood cells or red blood cell precursor cells.

31. The sgRNA according to claim 29, wherein the target sequence is the promoter of HBG1 or HBG2.

32. A single-base gene editing system, wherein the system comprises the fusion protein according to claim 1, and a sgRNA, wherein the sgRNA guides the fusion protein to conduct single-base gene editing on a target gene in a target cell.

33. The single-base gene editing system according to claim 32, wherein the target sequence of the sgRNA comprises at least one of SEQ ID NO: 17-36;

or, the cells are T cells, hematopoietic stem cells, bone marrow cells, red blood cells or a red blood cell precursor cells, or, the target sequence is at the promotor the promoter of HBG1 or HBG2.

34. A method for preparing a product for gene editing, treating or preventing disease, animal model or new plant variety, which comprises using the fusion protein according to claim 1 to conduct gene editing in a subject, an animal or a plant, wherein the disease is beta-hemoglobinopathy or Duchenne muscular dystrophy (DMD).

35. The method according to claim 34, wherein the beta-hemoglobinopathy comprises beta-thalassemia or sickle cell anemia.

36. A method for single-base gene editing, which comprises the steps of introducing the fusion protein according to claim 1 and the sgRNA into cells to edit target gene, wherein the sgRNA guides the fusion protein to conduct single-base gene editing on target gene in target cell.

37. The method according to claim 36, wherein the target sequence of the sgRNA comprises at least one of SEQ ID NO: 17-36;

or, the cells are T cells, hematopoietic stem cells, bone marrow cells, red blood cells or red blood cell precursor cells;

or, the target sequence is the promoter of HBG1 or HBG2.

38. A method for constructing animal models of disease, which comprises the steps of introducing the fusion protein according to claim 1 and the sgRNA into animal cells to conduct gene editing of the target gene, and creating animal cells bearing the disease or an animal bearing the disease.

39. The method according to claim 38, wherein the target sequence of the sgRNA comprises SEQ ID NO: 35, and the target gene comprises an HBG gene.

40. The method according to claim 38, wherein the target sequence of the sgRNA comprises the sequence of SEQ ID NO: 36, and the target gene comprises a DMD gene.

41. The method according to claim 38, wherein the animals are mammals, or, the cells are embryonic cells, or, the method of introduction is one or any combination of vector transformation, microinjection, transfection, lipid transfection, heat shock, electroporation, transduction, gene gun, and DEAE-dextran mediated transfer, or, the introduction is carried out using mRNA of the fusion protein according to claim 1 and the sgRNA.

42. The method according to claim 41, wherein the animals are rats or mice;

or, when the method of introduction is microinjection, the concentration of the mRNA of the fusion protein according to claim 1 for introduction is 1-1,000 ng/µL.

43. The method according to claim 42, wherein the concentration ratio of the mRNA of the fusion protein according to claim 1 to the sgRNA used for introduction is 1:(5-1).

44. A method for treating beta-hemoglobinopathy or Duchenne muscular dystrophy (DMD), comprising:

administering to a subject in need thereof a delivery vector of the gene encoding the fusion protein according to claim 1 and a sgRNA.

45. A product for treating beta-hemoglobinopathy or Duchenne muscular dystrophy (DMD), which comprises: delivery vector of the gene encoding the fusion protein according to claim 1 and a sgRNA, wherein the sgRNA guides the fusion protein to conduct single-base gene editing on the target gene in the target cell; and the target sequence is the promoter of HBG1 or HBG2, or the target gene is DMD gene.

46. The product according to claim 45, wherein the beta-hemoglobinopathy comprises beta thalassemia or sickle cell anemia;

or the cells are T cells, hematopoietic stem cells, bone marrow cells, red blood cells or red blood cell precursor cells.

47. The product according to claim 45, wherein the delivery vector comprises a viral vector or a non-viral vector;

wherein the viral vector comprises an adeno-associated viral vector, an adenoviral vector, a lentiviral vector, a retroviral vector or an oncolytic virus vector; and the non-viral vector comprises a cationic high-molecular polymer or a liposome.

48. A fusion protein for improving gene editing efficiency, comprising functional domain of a single-stranded DNA binding protein, a nucleoside deaminase and a nuclease;

wherein the nucleoside deaminase is located at the N terminal of the nuclease;

wherein the functional domain of the single-stranded DNA binding protein is located between the nucleoside deaminase and the nuclease; and wherein the single-stranded DNA binding protein is Rad51.

49. A fusion protein for improving gene editing efficiency, comprising functional domain of a single-stranded DNA binding protein, a nucleoside deaminase and a nuclease;

wherein the nucleoside deaminase is located at the N terminal of the nuclease;

wherein the functional domain of the single-stranded DNA binding protein is located between the nucleoside deaminase and the nuclease; and wherein the single-stranded DNA binding protein is RPA70.

* * * * *